US010098939B2

(12) United States Patent
Schneck et al.

(10) Patent No.: US 10,098,939 B2
(45) Date of Patent: Oct. 16, 2018

(54) REAGENTS AND METHODS FOR IDENTIFYING, ENRICHING, AND/OR EXPANDING ANTIGEN-SPECIFIC T CELLS

(71) Applicant: THE JOHNS HOPKINS UNIVERSITY, Baltimore, MD (US)

(72) Inventors: Jonathan Schneck, Silver Spring, MD (US); Karlo Perica, Baltimore, MD (US); Joan Glick Bieler, Silver Spring, MD (US); Mathias Oelke, Parkville, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/790,787

(22) Filed: Oct. 23, 2017

(65) Prior Publication Data

US 2018/0043003 A1 Feb. 15, 2018

Related U.S. Application Data

(63) Continuation of application No. 15/512,234, filed as application No. PCT/US2015/050593 on Sep. 17, 2015.

(60) Provisional application No. 62/051,660, filed on Sep. 17, 2014, provisional application No. 62/170,541, filed on Jun. 3, 2015.

(51) Int. Cl.

| | |
|---|---|
| *A61K 39/00* | (2006.01) |
| *B03C 1/01* | (2006.01) |
| *C12N 5/06* | (2006.01) |
| *B03C 1/28* | (2006.01) |
| *G01N 33/50* | (2006.01) |
| *G01N 33/569* | (2006.01) |
| *C12N 5/0783* | (2010.01) |
| *C12N 13/00* | (2006.01) |

(52) U.S. Cl.
CPC ............ *A61K 39/0011* (2013.01); *B03C 1/01* (2013.01); *B03C 1/288* (2013.01); *C12N 5/0637* (2013.01); *C12N 5/0638* (2013.01); *C12N 13/00* (2013.01); *G01N 33/505* (2013.01); *G01N 33/5011* (2013.01); *G01N 33/56972* (2013.01); *A61K 2039/5158* (2013.01); *A61K 2039/572* (2013.01); *B03C 2201/18* (2013.01); *B03C 2201/20* (2013.01); *G01N 2333/70539* (2013.01)

(58) Field of Classification Search
CPC ............ A61K 39/00; B03C 1/01; C12N 5/06
USPC .................................................... 424/277.1
See application file for complete search history.

(56) References Cited

U.S. PATENT DOCUMENTS

| | | |
|---|---|---|
| 6,015,884 A | 1/2000 | Schneck et al. |
| 6,140,113 A | 10/2000 | Schneck et al. |
| 6,268,411 B1 | 7/2001 | Schneck et al. |
| 6,448,071 B1 | 9/2002 | Schneck et al. |
| 6,458,354 B1 | 10/2002 | Schneck et al. |
| 6,734,013 B2 | 5/2004 | Schneck et al. |
| 6,797,514 B2 | 9/2004 | Berenson et al. |
| 6,867,041 B2 | 3/2005 | Berenson et al. |
| 6,905,874 B2 | 6/2005 | Berenson et al. |
| 7,973,137 B1 | 7/2011 | Schneck et al. |
| 2002/0131960 A1 | 9/2002 | Sadelain et al. |
| 2004/0115216 A1 | 6/2004 | Schneck et al. |
| 2010/0008920 A1 | 1/2010 | Schneck et al. |
| 2010/0284965 A1 | 11/2010 | Fahmy et al. |
| 2011/0293637 A1 | 12/2011 | Hacohen et al. |
| 2015/0366991 A1 | 12/2015 | Schneck et al. |
| 2016/0051698 A1 | 2/2016 | Schneck et al. |

OTHER PUBLICATIONS

Gura (Science. 1997; 278: 1041-1042).*
Dennis (Nature. Aug. 7, 2006; 442: 739-741).*
Reagan-Shaw et al. (FASEB J, 2007, 22: 659-61).*
Seruga et al. (2015, Clin Cancer Res, 21:4554-60).*
Montagna et al. (Cytotherapy, 2012, 14: 80-90).*
Zappasodi, et al., "The effect of artificial antigen-presenting cells with preclustered anti-CD28I-CD3/-LFA-1 monoclonal antibodies on the induction of ex vivo expansion of functional human antitumor T cells," Haematologica, 2008, vol. 93, No. 10, pp. 1523-1534.
Greten, et al., Development and Use of Multimeric Major Histocompatibility Complex Molecules, Clinical and Diagnostic Laboratory Immunology, 2002, pp. 216-220.
Chiu et al., "HLA-lg Based Artificial Antigen Presenting Cells for Efficient ex vivo Expansion of Human CTL." JOVE, 2011, 50, e2801, p. 1 of 5.
Quintarelli, et al., "Cytotoxic T lymphocytes directed to the preferentially expressed antigen of melanoma (PRAME) target chronic myeloid leukemia," Blood, 2008, vol. 112, No. 5, pp. 1876-1885.
Turtle, et al., "Artificial Antigen Presenting Cells for use in Adoptive Immunotherapy," Cancer J., 2010, vol. 16, No. 4, pp. 374-381.
Perica, et al., "Nanoscale artificial antigen presenting cells for T cell immunitherapy", Nanomedicine, Epub. Jul. 24, 2013, vol. 10 No. 1 pp. 119-129.
Perica, et al., "Magnetic field-induced T cell receptor clustering by nanoparticles enhances T cell activation and stimulates antitumor activity", ACS Nano, Epub. Feb. 24, 2014, vol. 8, No. 3, pp. 2252-2260.
International Search Report and Written Opinion of PCT/US2015/050593, dated Dec. 31, 2015, 18 pages.
Grant et al., Cell therapies for hematological malignancies: don't forget non-gene-modified t cells!: Blood Reviews, 2017, pp. 1-22.

(Continued)

*Primary Examiner* — Yan Xiao
(74) *Attorney, Agent, or Firm* — Morgan, Lewis & Bockius LLP

(57) ABSTRACT

Antigen-specific T cells, including nave T cells, and including rare precursor cells are enriched and expanded in culture. Enrichment and expansion provides a platform for more effective immunotherapy by adoptive transfer, as well as platforms for personalizing immunotherapy by determining T cell reactivity with a library of candidate peptide antigens.

20 Claims, 7 Drawing Sheets

(56) References Cited

OTHER PUBLICATIONS

Lam, et al., "Broadly-specific Cytotoxic T Cells Targeting Multiple HIV Antigens Are Expanded From HIV+ Patients: Implications for Immunotherapy," Molecular Therapy, 2015, vol. 23, No. 2, pp. 387-395.

Pollack et al., "Tetramer guided, cell sorter assisted production of clinical grade autologous NY-ESO-1 specific CD8+ T cells," Journal for ImmunoTherapy of Cancer, 2014, vol. 2, No. 36, pp. 1-10.

Rosenberg et al., "Adoptive cell transfer as personalized immunotherapy for human cancer," Science, 2015, vol. 348, Issue 6230, pp. 62-68.

Weber, et al., Generation of Tumor Antigen-Specific T Cell Lines from Pediatric Patients with Acute Lymphoblastic Leukemia—Implications for Immunotherapy, Clin Cancer Res; 2013, vol. 19, No. 18, pp. 5079-5091.

Wölfl, et al., "Antigen-specific activation and cytokine-facilitated expansion of naive, human CD8+ T cells," Nat Protoc. 2014, vol. 9, No. 4, pp. 950-966.

Yao, et al., "Increased PRAME-Specific CTL Killing of Acute Myeloid Leukemia Cells by Either a Novel Histone Deacetylase Inhibitor Chidamide Alone or Combined Treatment with Decitabine," PLOS ONE, 2013, vol. 8, No. 8, pp. 1-13.

\* cited by examiner

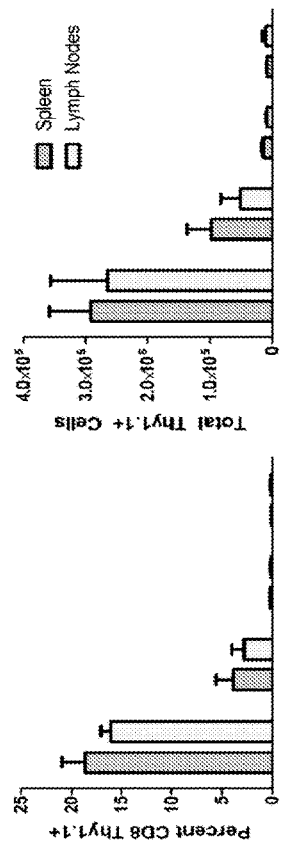
Fig. 4A
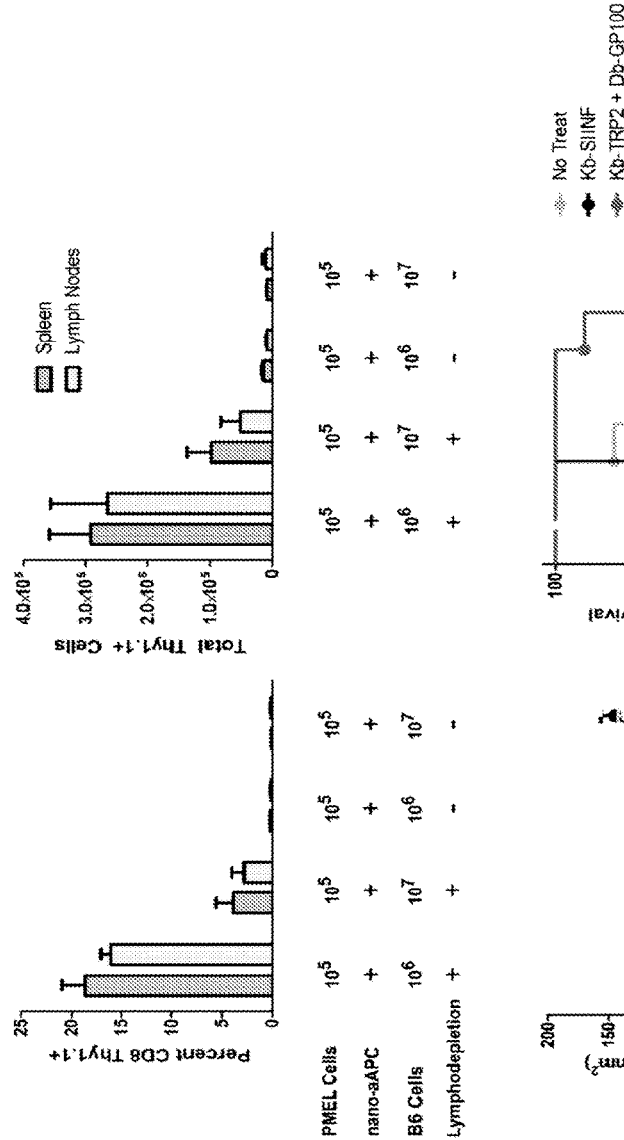
Fig. 4B
Fig. 4C
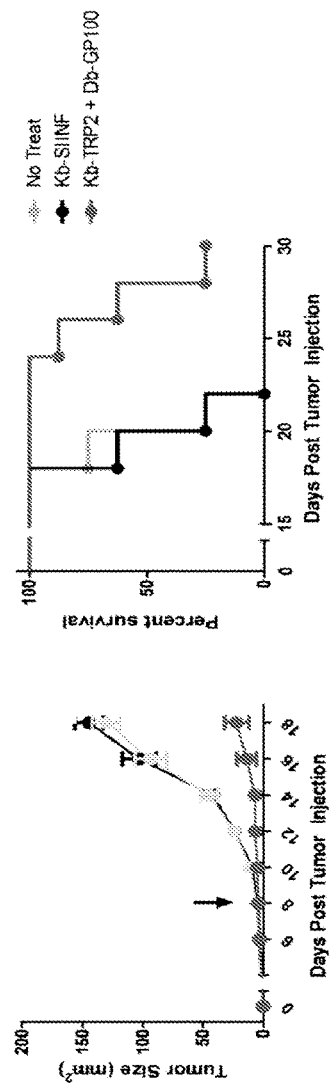
Fig. 4D

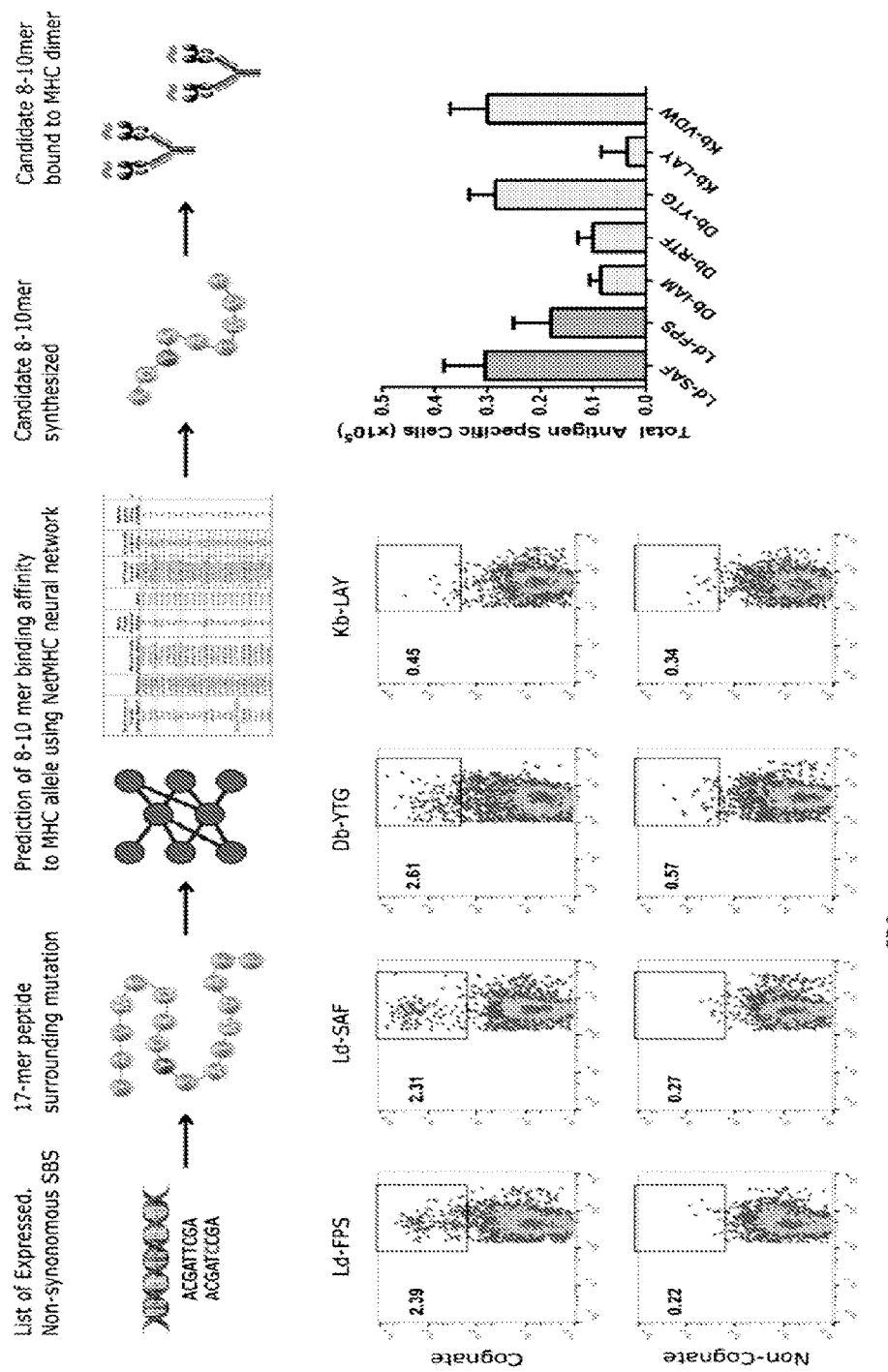

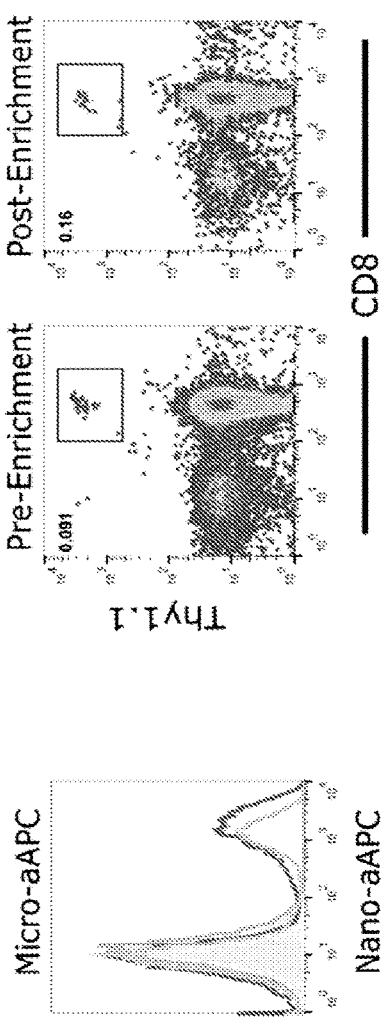
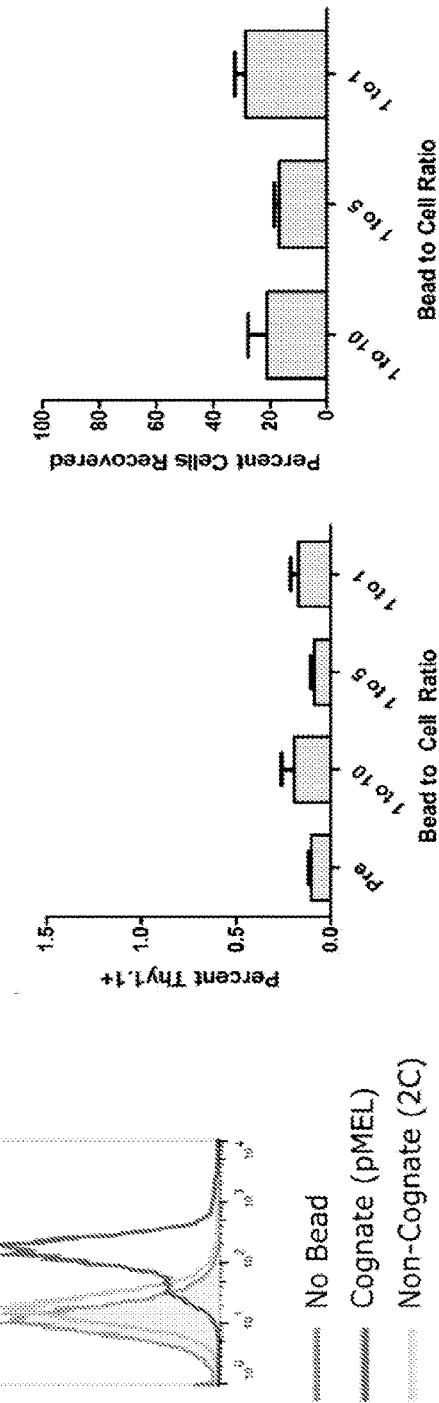
Fig. 7A
Fig. 7B
Fig. 7C

REAGENTS AND METHODS FOR IDENTIFYING, ENRICHING, AND/OR EXPANDING ANTIGEN-SPECIFIC T CELLS

TECHNICAL FIELD

The subject matter of this application relates to immunotherapy, and is related to the subject matter disclosed in PCT/US2014/25889 filed Mar. 13, 2014, the contents of which are incorporated by reference.

BACKGROUND

Expansion of antigen-specific T cells is complicated by the rarity of antigen-specific naive precursors, which can be as few as one per million. To generate the large numbers of tumor-specific T cells (for example) required for adoptive therapy, lymphocytes are conventionally stimulated with antigen over many weeks, often followed by T cell selection and sub-cloning in a labor intensive process.

There is a need for technologies that can quickly generate large numbers and high frequencies of antigen-specific T cells from naive precursors, or quickly identify T cell responses to candidate peptide antigens, for both therapeutic and diagnostic purposes.

SUMMARY OF THE INVENTION

In various aspects, the invention provides for rapid enrichment and expansion of antigen-specific T cells in culture, including from naïve T cells, and including from rare precursor cells. The invention thereby provides a platform for more effective immunotherapy (e.g., by adoptive transfer). The invention further provides platforms for rapidly identifying antigen-specific T cell responses from patient lymphocytes, and platforms for personalizing immunotherapy, by determining T cell reactivity against a library of candidate peptide antigens.

The invention employs in various embodiments nano-scale artificial Antigen Presenting Cells (aAPCs), which capture and deliver stimulatory signals to immune cells, such as antigen-specific T lymphocytes, such as CTLs. Signals present on the aAPCs can include Signal 1, antigenic peptide presented in the context of Major Histocompatibility Complex (MHC) (class I or class II); and Signal 2, one or more co-stimulatory ligands that modulate T cell response. Signal 2 in some embodiments is a ligand that binds and activates through CD28. In various embodiments, the particle material is paramagnetic and is preferably biocompatible, such as dextran-coated iron oxide particles. Paramagnetic particles allow for magnetic capture or "enrichment" by application of a magnetic field, as well as activation and subsequent expansion of antigen-specific lymphocytes within the enriched cell fraction, which is also enhanced by application of a magnetic field.

In some aspects, the invention provides a method for preparing an antigen-specific T-cell population. The method comprises providing a sample comprising T-cells from a patient. In some embodiments the patient is in need of adoptive transfer of antigen-specific T-cells. The sample may be a PBMC sample, or sample obtained by leukapheresis. The sample can be enriched for T cells of interest, such as CD8+ T cells and/or naïve T cells. The sample containing the T cells is contacted with a population of paramagnetic aAPCs presenting antigens that are common for the disease of interest (e.g., tumor-type), and/or presenting one or more antigens selected on a personalized basis. In certain embodiments, each aAPC bead presents a single antigen, and a cocktail of aAPC beads each presenting different antigens is used for enrichment/expansion. The paramagnetic property is used to capture or "enrich" the sample for antigen-specific T-cells, by placing a magnet within proximity to thereby separate aAPC-associated cells from non-associated cells. Recovered T-cells can be expanded in vitro by culture with the aAPCs, and expansion of antigen-specific cells is further enhanced by the presence of a magnetic field. The enrichment and expansion process may be repeated one or more times, for optimal expansion (and further purity) of antigen-specific cells.

In certain embodiments, the method provides for about 1000-10,000 fold expansion (or more) of antigen-specific T cells, with more than about $10^8$ antigen-specific T cells being generated in the span of, for example, 1-3 weeks. The resulting cells can be administered to the patient to treat disease. Antigen-specific frequency is an independently important parameter for optimal expansion after transfer, since competition for growth signals from irrelevant, co-transferred cells may significantly attenuate homeostatic expansion of anti-tumor T cells of interest.

In still other aspects, the invention provides methods for selecting T cell antigens on a personalized basis. For example, an array or library of aAPCs each presenting a candidate antigenic peptide, is screened with T cells from a subject or patient, and the response of the T cells to each aAPC-peptide is determined or quantified. T cell responses can be quantified, for example, by cytokine expression or expression of other surrogate marker of T cell activation. Exemplary assays platforms include immunochemistry, such as ELISA, or amplification of expressed genes, e.g., by RT-PCR. In other embodiments, T cell activation is quantified by measuring an intracellular signaling event that is indicative of T cell activation, such as calcium signaling. Such assays can employ any variety of colorimetric assays known in the art.

Peptide antigens showing the most robust responses are selected for immunotherapy, including in some embodiments adoptive immunotherapy, which may be achieved through enrichment and expansion of antigen-specific T cells. In some embodiments, and particularly for cancer immunotherapy, a patient's tumor is genetically analyzed, and tumor antigens are predicted from the patient's unique tumor mutation signature. These predicted antigens ("neoantigens") are synthesized and screened against the patient's T cells using the aAPC platform. Once reactive antigens are identified/confirmed, aAPCs can be prepared for the enrichment and expansion protocol described herein, or the aAPCs can be directly administered to the patient in some embodiments.

In some embodiments, a patient or subject's T cells are screened against an array or library of paramagnetic aAPCs, each presenting a different candidate peptide antigen. This screen can provide a wealth of information concerning the subject or patient's T cell repertoire, and the results are useful for diagnostic or prognostic purposes. For example, the number and identity of T cell anti-tumor responses against mutated proteins, overexpressed proteins, and/or other tumor-associated antigens can be used as a biomarker to stratify risk, to monitor efficacy of immunotherapy, or predict outcome of immunotherapy treatment. Further, the number or intensity of such T cell responses may be inversely proportionate to the risk of disease progression or may be predictive of resistance or non-responsiveness to chemotherapy. In other embodiments, a subject's or patient's T cells are screened against an array or library of nano-APCs each presenting a candidate peptide antigen, and the presence of T cells responses, or the number or intensity of these T cells responses, provides information concerning the health of the patient, for example, by identifying autoimmune disease, or identifying that the patient has a subclinical tumor. In these embodiments, the process not only identifies a potential disease state, but provides an initial understanding of the disease biology.

The present invention thereby provides for diagnostic and therapeutic advances in a number of T cell-related diseases or conditions, including cancer, autoimmune disease, and other diseases in which detection, enrichment, activation, and/or expansion of antigen-specific immune cells ex vivo is therapeutically or diagnostically desirable.

Further aspects and embodiments of the invention will be apparent to the skilled artisan based on the following detailed description.

DESCRIPTION OF THE FIGURES

(FIG. 1A) an embodiment of a nanoscale artificial antigen presenting cell (nano-aAPC) is synthesized by coupling MHC-Ig dimer (Signal 1) and a co-stimulatory anti-CD28 antibody (Signal 2) to a 50-100 nm iron-dextran nanoparticle. (FIG. 1B) Schematic of magnetic enrichment. Antigen-specific CD8+ T cells bound to nano-aAPC are retained in a magnetic column in the "enrichment" step, while non-cognate cells are less likely to bind. Enriched T cells are then activated by nano-aAPC and proliferate in the "expansion" step.

(FIG. 2A) Nano-aAPC mediate antigen-specific enrichment of cognate, Thy1.1+ pmel cells from a pool of thousand-fold more polyclonal, Thy1.2+ B6 splenocytes. (FIG. 2B) Summary of antigen-specific cell frequency and percent cells recovered after pmel enrichment performed as in (FIG. 2A) with increasing amounts of nano-aAPC. (FIG. 2C) Enrichment of endogenous Db-gp100 splenocytes by nano-aAPC (top). Frequency of non-cognate Kb-Trp2 cells does not increase after enrichment (bottom).

(FIG. 3A) Schematic of cell fractions used to assess the effect of enrichment on expansion. Particle-bound antigen-specific T cells are captured in a magnetic column (positive fraction), whereas unbound cells pass through (negative fraction). The negative fraction can be added back to the positive fraction to undo the effect of enrichment (positive+negative). (FIG. 3B) Increased frequency of antigen-specific cells generated after seven days of culture as a result of enrichment with Kb-Trp2 nano-aAPC. Negative (left), positive (middle) and positive+negative (right) fractions were cultured for seven days, then stained with cognate Kb-Trp2 (top) and control Kb-SIINF (bottom) dimer. (FIG. 3C) 10-15 fold increase in frequency of Kb-Trp2 cells (*, p<0.001 by t-test) when cells are enriched. (FIG. 3D) Representative FACS plots of Db-gp100, Kb-SIINF, and Ld-A5 nano-aAPC expansion seven days after enrichment with cognate nano-aAPC. (FIG. 3E) Summary of percent antigen-specific cells (left) and total antigen specific cells (right) after enrichment and activation with indicated nano-aAPC. (FIG. 3F) Three antigens (Db-gp100, Kb-SIINF, Kb-Trp2) enriched and expanded simultaneously. Representative FACS plots of antigen-specificity for each antigen from the same T cell culture. (FIG. 3G) Comparison of antigen-specificity (left) and total antigen-specific cells (right) generated for the three indicated antigens when enriched and expanded individually or together.

FIGS. 4A-4D: Adoptive Transfer of enriched and expanded T Cells Mediates Tumor Rejection. (FIG. 4A) Effect of lymphodepletion and decreased bystander competition on expansion after adoptive transfer. B6 mice were untreated or lymphodepleted with 500 cGy gamma radiation one day prior to adoptive transfer of $10^5$ pmel T cells in the presence of either $10^6$ or $10^7$ irrelevant B6 cells. Both lymphodepletion and administration of fewer bystander cells increased the frequency of pmel T cells recovered from spleen and lymph nodes (p<0.01 by two-way ANOVA). (FIG. 4B) Total number of Thy1.1+ pmel cells recovered in (FIG. 4A). (FIG. 4C) Kb-Trp2 and Db-gp100 Enriched+Expanded lymphocytes cultured for 7 days prior to adoptive transfer inhibited melanoma growth (p<0.01 by two-way ANOVA, 8 mice/group). Mice were injected with subcutaneous melanoma eight days prior and irradiated with 500 cGy gamma irradiation one day prior. Non-cognate enriched and expanded lymphocytes (SIINF) did not inhibit tumor growth (compared to untreated), whereas cognate enriched and expanded (Trp2+gp100) did. (FIG. 4D) Survival of animals from (FIG. 4C). 2/8 mice showed complete rejection of tumors in the Kb-Trp2 and Db-gp100 treated group, which had significantly longer survival compared to non-cognate and untreated groups (p<0.01 by Mantel-Cox).

(FIG. 5A) Representative staining and frequency of A2-NY-ESO1 (top) and A2-MART1 (bottom) specific cells immediately after CD8 isolation (Day 0, left) and after one week of enrichment and expansion (Day 7, right). (FIG. 5B) Summary of percent antigen-specific cell frequency (top) and total antigen specific cells (bottom) after enrichment/expansion with indicated nano-aAPC. Results derived from three experiments with different donors.

FIGS. 6A-6C: Neo-Epitope Expansion. (FIG. 6A) Schematic of process for generating candidate peptides for B16 and CT26 mutomes. 17-mer sequences surrounding single-base pair substitutions (SBS) are assessed for MHC binding by MHCNet prediction algorithm. (FIG. 6B) Representative binding of cells expanded with nano-aAPC E+E for seven days against neo-epitopes to cognate (top) and non-cognate (bottom) MHC. FIG. 6C) Total neo-epitope specific cells obtained at one week after E+E.

FIGS. 7A-7C: Micro-aAPC Are Not Effective For Antigen-Specific Enrichment. (FIG. 7A) Binding of Micro- (top) and Nano- (bottom) aAPC to cognate pMEL (red) or non-cognate 2C (blue) CD8+ T cells, characterized by fluorescent labeling of bound beads. No bead (grey) background is shown as control. (FIG. 7B) Micro-aAPC do not enrich cognate cells. Thy1.1+ pmel cells were incubated at a 1:1000 ratio with polyclonal, Thy1.2+ B6 splenocytes, and enrichment was attempted using Db-GP100 microparticles. Frequency of Thy1.1+ cells did not significantly increase after enrichment. (FIG. 7C) Antigen-specific cell frequency and percent of cells recovered, performed as in (FIG. 7C with increasing amounts of micro-aAPC.

DETAILED DESCRIPTION OF THE INVENTION

Figures 1A, 1B:
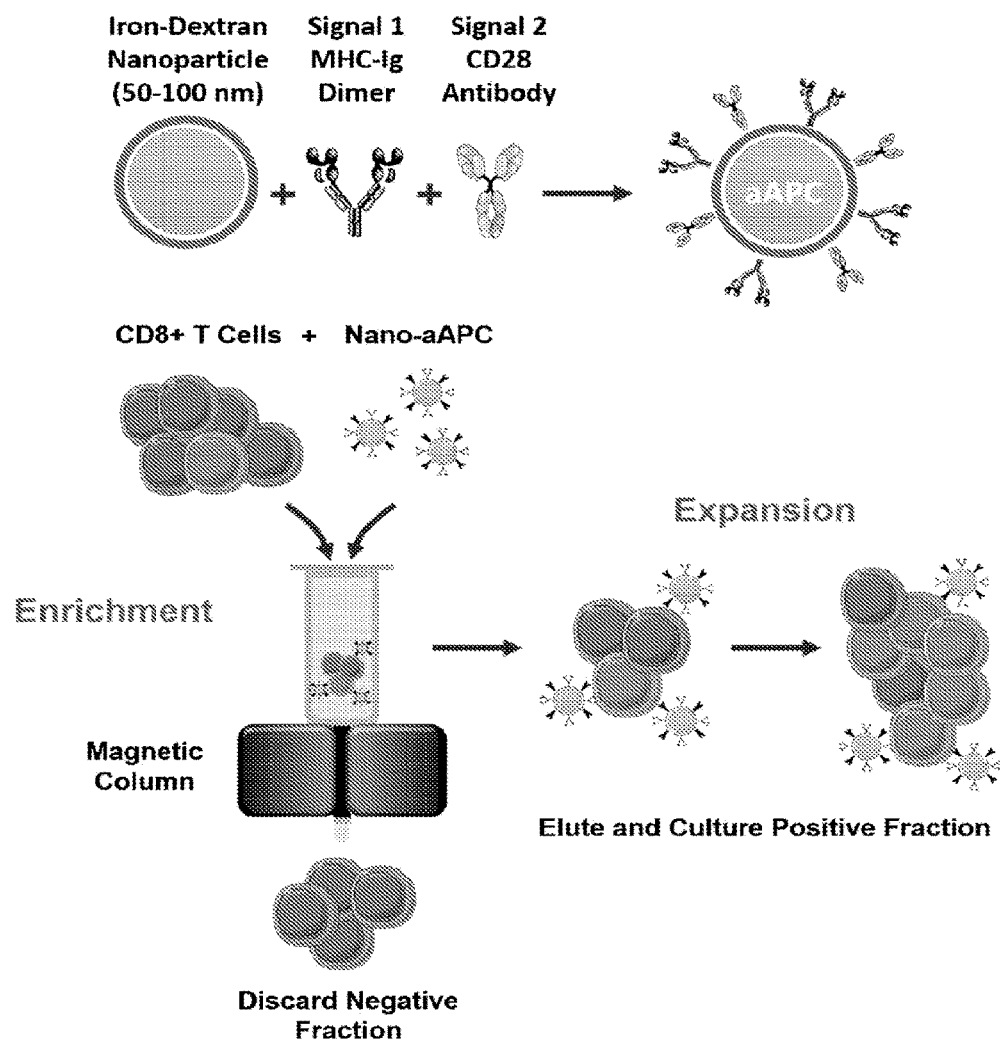
FIGS. 1A-B present schematics of an embodiment for enrichment and expansion of antigen-specific T cells.

Adoptive immunotherapy involves the activation and expansion of immune cells ex vivo, with the resulting cells transferred to the patient to treat disease, such as cancer.

Induction of antigen-specific cytotoxic (CD8+) lymphocyte (CTL) responses, for example, through adoptive transfer could be an attractive therapy, if sufficient numbers and frequency of activated and antigen-specific CTL can be generated in a relatively short time, including from rare precursor cells. This approach in some embodiments could even generate long-term memory that prevents recurrence of disease. In addition to cancer immunotherapy, and immunotherapies involving CTLs, the invention finds use with other immune cells, including CD4+ T cells and regulatory T cells, and thus is broadly applicable to immunotherapy for infectious disease and auto-immune disease, among others.

In one aspect, the present invention provides artificial Antigen Presenting Cells (aAPCs), which capture and deliver stimulatory signals to immune effector cells, such as antigen-specific T lymphocytes, such as CTLs. In some embodiments, these aAPCs offer a powerful tool for adoptive immunotherapy. Signals present on the aAPCs that support T cell activation include Signal 1, antigenic peptide presented in the context of Major Histocompatibility Complex (MHC), class I or class II, and which bind antigen-specific T-cell Receptors (TCR); and Signal 2, one or more co-stimulatory ligands that modulate T cell response. In some embodiments of this system, Signal 1 is conferred by a monomeric, dimeric or multimeric MHC construct. A dimeric construct is created in some embodiments by fusion to a variable region or $C_H1$ region of an immunoglobulin heavy chain sequence. The MHC complex is loaded with one or more antigenic peptides, and Signal 2 is either B7.1 (the natural ligand for the T cell receptor CD28) or an activating antibody against CD28. Both ligands may be directly chemically coupled to the surface of a microscale (4.5 µm) or nanoscale bead to create an artificial Antigen Presenting Cell (aAPC). In some embodiments, the particle material is paramagnetic, allowing for magnetic capture or "enrichment" by application of a magnetic field, as well as subsequent expansion of antigen-specific lymphocytes within the enriched cell fraction, which is also enhanced by application of a magnetic field. In other embodiments, the paramagnetic property supports a rapid T cell response (e.g., activation), even from naïve cells, which can be detected within minutes to hours in vitro.

In some aspects, the invention provides a method for preparing an antigen-specific T-cell population for adoptive transfer. The method comprises providing a sample comprising T-cells from a patient, where the patient is in need of adoptive transfer of antigen-specific T-cells. The T cells, or sample containing the T cells, are contacted with a population of paramagnetic aAPCs as described in detail herein, each of which presents a peptide antigen of interest in the context of MHC (class I or II), and thereby binds antigen-specific T-cells in the sample (including naïve antigen-specific cells that are infrequently represented). The aAPCs may present antigens that are common for the disease of interest (e.g., tumor-type), or may present one or more antigens selected on a personalized basis. The paramagnetic property can be used to capture or "enrich" the sample for antigen-specific T-cells, for example, by using a magnet to separate aAPC-associated cells from non-associated cells. Recovered T-cells, for example, those that remain associated with the paramagnetic aAPC particles, can be expanded in vitro in the presence of the aAPCs, and expansion of antigen-specific cells is further enhanced by the presence of a magnetic field. Without wishing to be bound by theory, it is believed that the paramagnetic aAPCs bound to the antigen-specific T cells will facilitate T cell receptor clustering in the presence of a magnetic field. The expansion step can proceed from about 3 days to about 2 weeks in some embodiments, or about 5 days to about 10 days (e.g., about 1 week). The enrichment and expansion process may then be repeated one or more times, for optimal expansion (and further purity) of antigen-specific cells. For subsequent rounds of enrichment and expansion, additional aAPCs may be added to the T cells to support expansion of the larger antigen-specific T cell population in the sample. In certain embodiments, the final round (e.g., round 2, 3, 4, or 5) of expansion occurs in vivo, where biocompatible nanoAPCs are added to the expanded T cell population, and then infused into the patient.

In certain embodiments, the method provides for about 1000-10,000 fold expansion (or more) of antigen-specific T cells, with more than about $10^8$ antigen-specific T cells being generated in the span of, for example, less than about one month, or less than about three weeks, or less than about two weeks, or in about one week. The resulting cells can be administered to the patient to treat disease. The aAPC may be administered to the patient along with the resulting antigen-specific T cell preparation in some embodiments.

In still other aspects, the invention provides methods for selecting T cell antigens on a personalized basis. For example, in certain embodiments an array or library of aAPCs each presenting a candidate antigenic peptide, is screened with T cells from a subject or patient (and in the presence of a magnetic field in some embodiments), and the response of the T cells to each aAPC-peptide is determined or quantified. T cell response can be quantified molecularly in some embodiments, for example, by quantifying cytokine expression or expression of other surrogate marker of T cell activation (e.g., by immunochemistry or amplification of expressed genes such as by RT-PCR). In some embodiments, the quantifying step is performed between about 15 hours and 48 hours in culture. In other embodiments, T cell response is determined by detecting intracellular signaling (e.g., Ca2+ signaling, or other signaling that occurs early during T cell activation), and thus can be quantified within about 15 minutes to about 5 hours (e.g., within about 15 minutes to about 2 hours) of culture with the nano-aAPCs. Peptides showing the most robust responses are selected for immunotherapy, including in some embodiments the adoptive immunotherapy approach described herein. In some embodiments, and particularly for cancer immunotherapy, a patient's tumor is genetically analyzed (e.g., using next generation sequencing), and tumor antigens are predicted from the patient's unique tumor mutation signature. These predicted antigens ("neoantigens") are synthesized and screened against the patient's T cells using the aAPC platform described herein. Once reactive antigens are identified/confirmed, aAPCs can be prepared for the enrichment and expansion protocol described herein, or the aAPCs can be directly administered to the patient in some embodiments.

In some aspects, a subject or patient's T cells are screened against an array or library of paramagnetic nano-aAPCs (as described herein), where each paramagnetic nano-aAPC presents a peptide antigen. T cell responses to each are determined or quantified as described herein, providing useful information concerning the patient's T cell repertoire, and hence the condition of the subject or patient.

For example, the number and identity of T cell anti-tumor responses against mutated proteins, overexpressed proteins, and/or other tumor-associated antigens can be used as a biomarker to stratify risk, and in some embodiments can involve a computer-implemented classifier algorithm to classify the response profile for drug resistance or drug sensitivity, or stratify the response profile as a candidate for immunotherapy (e.g., checkpoint inhibitor therapy or adoptive T cell transfer therapy). For example, the number or intensity of such T cell responses may be inversely proportionate to a high risk of disease progression, and/or may directly relate to the patient's likely response to immunotherapy, which may include one or more of checkpoint inhibitor therapy, adoptive T cell transfer, or other immunotherapy for cancer.

In still other aspects and embodiments, the patient's T cells are screened against an array or library of paramagnetic nano-APCs, each presenting a candidate peptide antigen. For example, the array or library may present tumor-associated antigens, or may present auto-antigens, or may present T cell antigens relating to various infectious diseases. By incubating the array or library with the patient's T cells, and in the presence of a magnetic field to encourage T cell receptor clustering, the presence of T cells responses, and/or the number or intensity of these T cells responses, can be rapidly determined. This information is useful for diagnosing, for example, a sub-clinical tumor, an autoimmune or immune disease, or infectious disease, and can provide an initial understanding of the disease biology, including, potential pathogenic or therapeutic T cells, T cell antigens, and an understanding of the T cell receptors of interest, which represent drug or immunotherapy targets.

Various alternative embodiments of the various aspects of the invention are described in detail below.

The present invention provides for immunotherapy for cancer and other diseases in which detection, enrichment and/or expansion of antigen-specific immune cells ex vivo is therapeutically or diagnostically desirable. The invention is generally applicable for detection, enrichment and/or expansion of antigen-specific T cells, including cytotoxic T lymphocytes (CTLs), helper T cells, and regulatory T cells.

In some embodiments, the patient is a cancer patient. The enrichment and expansion of antigen-specific CTLs ex vivo for adoptive transfer to the patient provides for a robust anti-tumor immune response. Cancers that can be treated or evaluated according to the methods include cancers that historically illicit poor immune responses or have a high rate of recurrence. Exemplary cancers include various types of solid tumors, including carcinomas, sarcomas, and lymphomas. In various embodiments the cancer is melanoma (including metastatic melanoma), colon cancer, duodenal cancer, prostate cancer, breast cancer, ovarian cancer, ductal cancer, hepatic cancer, pancreatic cancer, renal cancer, endometrial cancer, testicular cancer, stomach cancer, dysplastic oral mucosa, polyposis, head and neck cancer, invasive oral cancer, non-small cell lung carcinoma, small-cell lung cancer, mesothelioma, transitional and squamous cell urinary carcinoma, brain cancer, neuroblastoma, and glioma. In some embodiments, the cancer is a hematological malignancy, such as chronic myelogenous leukemia, childhood acute leukemia, non-Hodgkin's lymphomas, chronic lymphocytic leukemia, malignant cutaneous T-cells, mycosis fungoids, non-MF cutaneous T-cell lymphoma, lymphomatoid papulosis, T-cell rich cutaneous lymphoid hyperplasia, and discoid lupus erythematosus.

In various embodiments, the cancer is stage I, stage II, stage III, or stage IV. In some embodiments, the cancer is metastatic and/or recurrent. In some embodiments, the cancer is preclinical, and is detected in the screening system described herein (e.g., colon cancer, pancreatic cancer, or other cancer that is difficult to detect early).

In some embodiments, the patient has an infectious disease. The infectious disease may be one in which enrichment and expansion of antigen-specific immune cells (such as CD8+ or CD4+ T cells) ex vivo for adoptive transfer to the patient could enhance or provide for a productive immune response. Infectious diseases that can be treated include those caused by bacteria, viruses, prions, fungi, parasites, helminths, etc. Such diseases include AIDS, hepatitis, CMV infection, and post-transplant lymphoproliferative disorder (PTLD). CMV, for example, is the most common viral pathogen found in organ transplant patients and is a major cause of morbidity and mortality in patients undergoing bone marrow or peripheral blood stem cell transplants. This is due to the immunocompromised status of these patients, which permits reactivation of latent virus in seropositive patients or opportunistic infection in seronegative individuals. A useful alternative to these treatments is a prophylactic immunotherapeutic regimen involving the generation of vims-specific CTL derived from the patient or from an appropriate donor before initiation of the transplant procedure. PTLD occurs in a significant fraction of transplant patients and results from Epstein-Barr virus (EBV) infection. EBV infection is believed to be present in approximately 90% of the adult population in the United States. Active viral replication and infection is kept in check by the immune system, but, as in cases of CMV, individuals immunocompromised by transplantation therapies lose the controlling T cell populations, which permits viral reactivation. This represents a serious impediment to transplant protocols. EBV may also be involved in tumor promotion in a variety of hematological and non-hematological cancers.

In some embodiments, the patient has an autoimmune disease, in which enrichment and expansion of regulatory T cells (e.g., CD4+, CD25+, Foxp3+) ex vivo for adoptive transfer to the patient could dampen the deleterious immune response. Autoimmune diseases that can be treated include systemic lupus erythematosus, rheumatoid arthritis, type I diabetes, multiple sclerosis, Crohn's disease, ulcerative colitis, psoriasis, myasthenia gravis, Goodpasture's syndrome, Graves' disease, pemphigus vulgaris, Addison's disease, dermatitis herpetiformis, celiac disease, and Hashimoto's thyroiditis. In some embodiments, the patient is suspected of having an autoimmune disease or immune condition (such as those described in the preceding sentence), and the evaluation of T cell responses against a library of paramagnetic nano-aAPCs as described herein, is useful for identifying or confirming the immune condition.

Thus, in various embodiments the invention involves enrichment and expansion of antigen-specific T cells, such as cytotoxic T lymphocytes (CTLs), helper T cells, or regulatory T cells. In some embodiments, the invention involves enrichment and expansion of antigen-specific CTLs. Precursor T cells can be obtained from the patient or from a suitable HLA-matched donor. Precursor T cells can be obtained from a number of sources, including peripheral blood mononuclear cells (PBMC), bone marrow, lymph node tissue, spleen tissue, and tumors. In some embodiments, the sample is a PBMC sample from the patient. In some embodiments, the PBMC sample is used to isolate the T cell population of interest, such as CD8+, CD4+ or regulatory T cells. In some embodiments, precursor T cells are obtained from a unit of blood collected from a subject using any number of techniques known to the skilled artisan, such as Ficoll separation. For example, precursor T cells from the circulating blood of an individual can be obtained by apheresis or leukapheresis. The apheresis product typically contains lymphocytes, including T cells and precursor T cells, monocytes, granulocytes, B cells, other nucleated white blood cells, red blood cells, and platelets. Leukapheresis is a laboratory procedure in which white blood cells are separated from a sample of blood.

Cells collected by apheresis can be washed to remove the plasma fraction and to place the cells in an appropriate buffer or media for subsequent processing steps. Washing steps can be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample can be removed and the cells directly re-suspended in a culture medium.

If desired, precursor T cells can be isolated from peripheral blood lymphocytes by lysing the red blood cells and depleting the monocytes, for example, by centrifugation through a PERCOLL™ gradient.

If desired, subpopulations of T cells can be separated from other cells that may be present. For example, specific subpopulations of T cells, such as CD28+, CD4+, CD8+, CD45RA+, and CD45RO+ T cells, can be further isolated by positive or negative selection techniques. Other enrichment techniques include cell sorting and/or selection via negative magnetic immunoadherence or flow cytometry, e.g., using a cocktail of monoclonal antibodies directed to cell surface markers present on the cells negatively selected.

In certain embodiments, leukocytes are collected by leukapheresis, and are subsequently enriched for CD8+ T cells using known processes, such as magnetic enrichment columns that are commercially available. The CD8-enriched cells are then enriched for antigen-specific T cells using magnetic enrichment with the aAPC reagent. In various embodiments, at least about $10^5$, or at least about $10^6$, or at least about $10^7$ CD8-enriched cells are isolated for antigen-specific T cell enrichment.

In various embodiments, the sample comprising the immune cells (e.g., CD8-F T cells) is contacted with an artificial Antigen Presenting Cell (aAPC) having magnetic properties. Paramagnetic materials have a small, positive susceptibility to magnetic fields. These materials are attracted by a magnetic field and the material does not retain the magnetic properties when the external field is removed. Exemplary paramagnetic materials include, without limitation, magnesium, molybdenum, lithium, tantalum, and iron oxide. Paramagnetic beads suitable for magnetic enrichment are commercially available (DYNABEADS™, MACS MICROBEADS™, Miltenyi Biotec). In some embodiments, the aAPC particle is an iron dextran bead (e.g., dextran-coated iron-oxide bead).

In certain embodiments, the aAPCs contain at least two ligands, an antigen presenting complex (peptide-MHC), and a lymphocyte activating ligand.

Antigen presenting complexes comprise an antigen binding cleft, which harbors an antigen for presentation to a T cell or T cell precursor. Antigen presenting complexes can be, for example, MHC class I or class II molecules, and can be linked or tethered to provide dimeric or multimeric MHC. In some embodiments, the MHC are monomeric, but their close association on the nano-particle is sufficient for avidity and activation. In some embodiments, the MHC are dimeric. Dimeric MHC class I constructs can be constructed by fusion to immunoglobulin heavy chain sequences, which are then associated through one or more disulfide bonds (and with associated light chains). In some embodiments, the signal 1 complex is a non-classical MHC-like molecule such as member of the CD1 family (e.g., CD1a, CD1b, CD1c, CD1d, and CD1e). MHC multimers can be created by direct tethering through peptide or chemical linkers, or can be multimeric via association with streptavidin through biotin moieties. In some embodiments, the antigen presenting complexes are MHC class I or MHC class II molecular complexes involving fusions with immunoglobulin sequences, which are extremely stable and easy to produce, based on the stability and secretion efficiency provided by the immunoglobulin backbone.

MHC class I molecular complexes having immunoglobulin sequences are described in U.S. Pat. No. 6,268,411, which is hereby incorporated by reference in its entirety. These MHC class I molecular complexes may be formed in a conformationally intact fashion at the ends of immunoglobulin heavy chains. MHC class I molecular complexes to which antigenic peptides are bound can stably bind to antigen-specific lymphocyte receptors (e.g., T cell receptors). In various embodiments, the immunoglobulin heavy chain sequence is not full length, but comprises an Ig hinge region, and one or more of CH1, CH2, and/or CH3 domains. The Ig sequence may or may not comprise a variable region, but where variable region sequences are present, the variable region may be full or partial. The complex may further comprise immunoglobulin light chains.

Exemplary MHC class I molecular complexes comprise at least two fusion proteins. A first fusion protein comprises a first MHC class I α chain and a first immunoglobulin heavy chain (or portion thereof comprising the hinge region), and a second fusion protein comprises a second MHC class I α chain and a second immunoglobulin heavy chain (or portion thereof comprising the hinge region). The first and second immunoglobulin heavy chains associate to form the MHC class I molecular complex, which comprises two MHC class I peptide-binding clefts. The immunoglobulin heavy chain can be the heavy chain of an IgM, IgD, IgG1, IgG3, IgG2β, IgG2α, IgG4, IgE, or IgA. In some embodiments, an IgG heavy chain is used to form MHC class I molecular complexes. If multivalent MHC class I molecular complexes are desired, IgM or IgA heavy chains can be used to provide pentavalent or tetravalent molecules, respectively.

Exemplary class I molecules include HLA-A, HLA-B, HLA-C, HLA-E, and these may be employed individually or in any combination. In some embodiments, the antigen presenting complex is an HLA-A2 ligand.

Exemplary MHC class II molecular complexes are described in U.S. Pat. No. 6,458,354, U.S. Pat. No. 6,015,884, U.S. Pat. No. 6,140,113, and U.S. Pat. No. 6,448,071, which are hereby incorporated by reference in their entireties. MHC class II molecular complexes comprise at least four fusion proteins. Two first fusion proteins comprise (i) an immunoglobulin heavy chain (or portion thereof comprising the hinge region) and (ii) an extracellular domain of an MHC class IIβ chain. Two second fusion proteins comprise (i) an immunoglobulin κ or λ light chain (or portion thereof) and (ii) an extracellular domain of an MHC class IIα chain. The two first and the two second fusion proteins associate to form the MHC class II molecular complex. The extracellular domain of the MHC class IIβ chain of each first fusion protein and the extracellular domain of the MHC class IIα chain of each second fusion protein form an MHC class II peptide binding cleft.

The immunoglobulin heavy chain can be the heavy chain of an IgM, IgD, IgG3, IgG1, IgG2β, IgG2α, IgG4, IgE, or IgA. In some embodiments, an IgG1 heavy chain is used to form divalent molecular complexes comprising two antigen binding clefts. Optionally, a variable region of the heavy chain can be included. IgM or IgA heavy chains can be used to provide pentavalent or tetravalent molecular complexes, respectively.

Fusion proteins of an MIIC class II molecular complex can comprise a peptide linker inserted between an immunoglobulin chain and an extracellular domain of an MHC class II polypeptide. The length of the linker sequence can vary, depending upon the flexibility required to regulate the degree of antigen binding and receptor cross linking.

Immunoglobulin sequences in some embodiments are humanized monoclonal antibody sequences.

Signal 2 is generally a T cell affecting molecule, that is, a molecule that has a biological effect on a precursor T cell or on an antigen-specific T cell. Such biological effects include, for example, differentiation of a precursor T cell into a CTL, helper T cell (e.g., Th1, Th2), or regulatory T cell; and/or proliferation of T cells. Thus, T cell affecting molecules include T cell costimulatory molecules, adhesion molecules, T cell growth factors, and regulatory T cell inducer molecules. In some embodiments, an aAPC comprises at least one such ligand; optionally, an aAPC comprises at least two, three, or four such ligands.

In certain embodiments, signal 2 is a T cell costimulatory molecule. T cell costimulatory molecules contribute to the activation of antigen-specific T cells. Such molecules include, but are not limited to, molecules that specifically bind to CD28 (including antibodies), CD80 (B7-1), CD86 (B7-2), B7-H3, 4-1BB, 4-1BBL, CD27, CD30, CD134 (OX-40L), B7h (B7RP-1), CD40, LIGHT, antibodies that specifically bind to HVEM, antibodies that specifically bind to CD40L, antibodies that specifically bind to OX40, and antibodies that specifically bind to 4-1BB. In some embodiments, the costimulatory molecule (signal 2) is an antibody (e.g., a monoclonal antibody) or portion thereof, such as $F(ab')_2$, Fab, scFv, or single chain antibody, or other antigen binding fragment. In some embodiments, the antibody is a humanized monoclonal antibody or portion thereof having antigen-binding activity, or is a fully human antibody or portion thereof having antigen-binding activity.

Adhesion molecules useful for nano-aAPC can be used to mediate adhesion of the nano-aAPC to a T cell or to a T cell precursor. Useful adhesion molecules include, for example, ICAM-1 and LFA-3.

In some embodiments, signal 1 is provided by peptide-HLA-A2 complexes, and signal 2 is provided by B7.1-Ig or anti-CD28. An exemplary anti-CD28 monoclonal antibody is 9.3 mAb (Tan et al., *J. Exp. Med.* 1993 177:165), which may be humanized in certain embodiments and/or conjugated to the bead as a fully intact antibody or an antigen-binding fragment thereof.

Some embodiments employ T cell growth factors, which affect proliferation and/or differentiation of T cells. Examples of T cell growth factors include cytokines (e.g., interleukins, interferons) and superantigens. If desired, cytokines can be present in molecular complexes comprising fusion proteins, or can be encapsulated by the aAPC. Particularly useful cytokines include IL-2, IL-4, IL-7, IL-10, IL-12, IL-15, IL-21 gamma interferon, and CXCL10. Optionally, cytokines are provided solely by media components during expansion steps.

The nanoparticles can be made of any material, and materials can be appropriately selected for the desired magnetic property, and may comprise, for example, metals such as iron, nickel, cobalt, or alloy of rare earth metal. Paramagnetic materials also include magnesium, molybdenum, lithium, tantalum, and iron oxide. Paramagnetic beads suitable for enrichment of materials (including cells) are commercially available, and include iron dextran beads, such as dextran-coated iron oxide beads. In aspects of the invention where magnetic properties are not required, nanoparticles can also be made of nonmetal or organic (e.g., polymeric) materials such as cellulose, ceramics, glass, nylon, polystyrene, rubber, plastic, or latex. In exemplary material for preparation of nanoparticles is poly(lactic-co-glycolic acid) (PLGA) and copolymers thereof, which may be employed in connection with these embodiments. Other materials including polymers and co-polymers that may be employed include those described in PCT/US2014/25889, which is hereby incorporated by reference in its entirety.

In some embodiments, the magnetic particles are biocompatible. This is particularly important in embodiments where the aAPC will be delivered to the patient in association with the enriched and expanded cells. For example, in some embodiments, the magnetic particles are biocompatible iron dextran paramagnetic beads.

In various embodiments, the particle has a size (e.g., average diameter) within about 10 to about 500 nm, or within about 20 to about 200 nm. Especially in embodiments where aAPC will be delivered to patients, microscale aAPC are too large to be carried by lymphatics, and when injected subcutaneously remain at the injection site. When injected intravenously, they lodge in capillary beds. In fact, the poor trafficking of microscale beads has precluded the study of where aAPC should traffic for optimal immunotherapy. Trafficking and biodistribution of nano-aAPC is likely to be more efficient than microscale aAPC. For example, two potential sites where an aAPC might be most effective are the lymph node, where naive and memory T cells reside, and the tumor itself. Nanoparticles of about 50 to about 200 nm diameter can be taken up by lymphatics and transported to the lymph nodes, thus gaining access to a larger pool of T cells. As described in PCT/US2014/25889, which is hereby incorporated by reference, subcutaneous injection of nano-aAPCs resulted in less tumor growth than controls or intravenously injected beads.

In some embodiments, re-enrichment of antigen-specific T cells using nano-sized aAPC, just prior to infusion of the T cells into the patient, will avoid blockage of veins and arteries, for example, which could be an effect if micro-sized aAPCs were infused into the patient along with cells.

Receptor-ligand interactions at the cell-nanoparticle interface are not well understood. However, nanoparticle binding and cellular activation are sensitive to membrane spatial organization, which is particularly important during T cell activation, and magnetic fields can be used to manipulate cluster-bound nanoparticles to enhance activation. See WO/2014/150132. For example, T cell activation induces a state of persistently enhanced nanoscale TCR clustering and nanoparticles are sensitive to this clustering in a way that larger particles are not. See WO/2014/150132.

Furthermore, nanoparticle interactions with TCR clusters can be exploited to enhance receptor triggering. T cell activation is mediated by aggregation of signaling proteins, with "signaling clusters" hundreds of nanometers across, initially forming at the periphery of the T cell-APC contact site and migrating inward. As described herein, an external magnetic field can be used to enrich antigen-specific T cells (including rare naïve cells) and to drive aggregation of magnetic nano-aAPC bound to TCR, resulting in aggregation of TCR clusters and enhanced activation of naïve T cells. Magnetic fields can exert appropriately strong forces on paramagnetic particles, but are otherwise biologically inert, making them a powerful tool to control particle behavior. T cells bound to paramagnetic nano-aAPC are activated in the presence of an externally applied magnetic field. Nano-aAPC are themselves magnetized, and attracted to both the field source and to nearby nanoparticles in the field, inducing bead and thus TCR aggregation to boost aAPC-mediated activation. See WO/2014/150132.

Nano-aAPCs bind more TCR on and induce greater activation of previously activated compared to naive T cells. In addition, application of an external magnetic field induces nano-aAPC aggregation on naive cells, enhancing T cells proliferation both in vitro and following adoptive transfer in vivo. Importantly, in a melanoma adoptive immunotherapy model, T cells activated by nano-aAPC in a magnetic field mediate tumor rejection. Thus, the use of applied magnetic fields permits activation of naive T cell populations, which otherwise are poorly responsive to stimulation. This is an important feature of immunotherapy as naive T cells have been shown to be more effective than more differentiated subtypes for cancer immunotherapy, with higher proliferative capacity and greater ability to generate strong, long-term T cell responses. Thus, nano-aAPC can used for magnetic field enhanced activation of T cells to increase the yield and activity of antigen-specific T cells expanded from naive precursors, improving cellular therapy for example, patients with infectious diseases, cancer, or autoimmune diseases, or to provide prophylactic protection to immuno-suppressed patients.

Molecules can be directly attached to nanoparticles by adsorption or by direct chemical bonding, including covalent bonding. See, Hermanson, BIOCONJUGATE TECHNIQUES, Academic Press, New York, 1996. A molecule itself can be directly activated with a variety of chemical functionalities, including nucicophilic groups, leaving groups, or electrophilic groups. Activating functional groups include alkyl and acyl halides, amines, sulfhydryls, aldehydes, unsaturated bonds, hydrazides, isocyanates, isothiocyanates, ketones, and other groups known to activate for chemical bonding. Alternatively, a molecule can be bound to a nanoparticle through the use of a small molecule-coupling reagent. Non-limiting examples of coupling reagents include carbodiimides, maleimides, n-hydroxysuccinimide esters, bischloroethylamines, bifunctional aldehydes such as glutaraldehyde, anyhydrides and the like. In other embodiments, a molecule can be coupled to a nanoparticle through affinity binding such as a biotin-streptavidin linkage or coupling, as is well known in the art. For example, streptavidin can be bound to a nanoparticle by covalent or non-covalent attachment, and a biotinylated molecule can be synthesized using methods that are well known in the art.

If covalent binding to a nanoparticle is contemplated, the support can be coated with a polymer that contains one or more chemical moieties or functional groups that are available for covalent attachment to a suitable reactant, typically through a linker. For example, amino acid polymers can have groups, such as the s-amino group of lysine, available to couple a molecule covalently via appropriate linkers. This disclosure also contemplates placing a second coating on a nanoparticle to provide for these functional groups.

Activation chemistries can be used to allow the specific, stable attachment of molecules to the surface of nanoparticles. There are numerous methods that can be used to attach proteins to functional groups. For example, the common cross-linker glutaraldehyde can be used to attach protein amine groups to an aminated nanoparticle surface in a two-step process. The resultant linkage is hydrolytically stable. Other methods include use of cross-linkers containing n-hydrosuccinimido (NHS) esters which react with amines on proteins, cross-linkers containing active halogens that react with amine-, sulfhydryl-, or histidine-containing proteins, cross-linkers containing epoxides that react with amines or sulfhydryl groups, conjugation between maleimide groups and sulfhydryl groups, and the formation of protein aldehyde groups by periodate oxidation of pendant sugar moieties followed by reductive amination.

The ratio of particular ligands on the same nanoparticle can be varied to increase the effectiveness of the nanoparticle in antigen or costimulatory ligand presentation. For example, nanoparticles can be coupled with HLA-A2-Ig and anti-CD28 at a variety of ratios, such as about 30:1, about 25:1, about 20:1, about 15:1, about 10:1, about 5:1, about 3:1, about 2:1, about 1:1, about 0.5:1, about 0.3:1; about 0.2:1, about 0.1:1, or about 0.03:1. The total amount of protein coupled to the supports may be, for example, about 250 mg/ml, about 200 mg/ml, about 150 mg/ml, about 100 mg/ml, or about 50 mg/ml of particles. Because effector functions such as cytokine release and growth may have differing requirements for Signal 1 versus Signal 2 than T cell activation and differentiation, these functions can be determined separately.

The configuration of nanoparticles can vary from being irregular in shape to being spherical and/or from having an uneven or irregular surface to having a smooth surface. Non-spherical aAPCs are described in WO 2013/086500, which is hereby incorporated by reference in its entirety.

The aAPCs present antigen to T cells and thus can be used to both enrich for and expand antigen-specific T cells, including from naïve T cells. The peptide antigens will be selected based on the desired therapy, for example, cancer, type of cancer, infectious disease, etc. In some embodiments, the method is conducted to treat a cancer patient, and neoantigens specific to the patient are identified, and synthesized for loading aAPCs. In some embodiments, between three and ten neoantigens are identified through genetic analysis of the tumor (e.g., nucleic acid sequencing), followed by predictive bioinformatics. As shown herein, several antigens can be employed together (on separate aAPCs), with no loss of functionality in the method. In some embodiments, the antigens are natural, non-mutated, cancer antigens, of which many are known. This process for identifying antigens on a personalized basis is described in greater detail below.

A variety of antigens can be bound to antigen presenting complexes. The nature of the antigens depends on the type of antigen presenting complex that is used. For example, peptide antigens can be bound to MHC class I and class II peptide binding clefts. Non-classical MHC-like molecules can be used to present non-peptide antigens such as phospholipids, complex carbohydrates, and the like (e.g., bacterial membrane components such as mycolic acid and lipoarabinomannan). Any peptide capable of inducing an immune response can be bound to an antigen presenting complex. Antigenic peptides include tumor-associated antigens, autoantigens, alloantigens, and antigens of infectious agents.

"Tumor-associated antigens" include unique tumor antigens expressed exclusively by the tumor from which they are derived, shared tumor antigens expressed in many tumors but not in normal adult tissues (oncofetal antigens), and tissue-specific antigens expressed also by the normal tissue from which the tumor arose. Tumor associated antigens can be, for example, embryonic antigens, antigens with abnormal post-translational modifications, differentiation antigens, products of mutated oncogenes or tumor suppressors, fusion proteins, or oncoviral proteins.

A variety of tumor-associated antigens are known in the art, and many of these are commercially available. Oncofetal and embryonic antigens include carcinoembryonic antigen and alpha-fetoprotein (usually only highly expressed in developing embryos but frequently highly expressed by tumors of the liver and colon, respectively), MAGE-1 and MAGE-3 (expressed in melanoma, breast cancer, and glioma), placental alkaline phosphatase sialyl-Lewis X (expressed in adenocarcinoma), CA-125 and CA-19 (expressed in gastrointestinal, hepatic, and gynecological tumors), TAG-72 (expressed in colorectal tumors), epithelial glycoprotein 2 (expressed in many carcinomas), pancreatic oncofetal antigen, 5T4 (expressed in gastriccarcinoma), alphafetoprotein receptor (expressed in multiple tumor types, particularly mammary tumors), and M2A (expressed in germ cell neoplasia).

Tumor-associated differentiation antigens include tyrosinase (expressed in melanoma) and particular surface immunoglobulins (expressed in lymphomas).

Mutated oncogene or tumor-suppressor gene products include Ras and p53, both of which are expressed in many tumor types, Her-2/neu (expressed in breast and gynecological cancers), EGF-R, estrogen receptor, progesterone receptor, retinoblastoma gene product, myc (associated with lung cancer), ras, p53, nonmutant associated with breast tumors, MAGE-1, and MAGE-3 (associated with melanoma, lung, and other cancers). Fusion proteins include BCR-ABL, which is expressed in chromic myeloid leukemia. Oncoviral proteins include HPV type 16, E6, and E7, which are found in cervical carcinoma.

Tissue-specific antigens include melanotransferrin and MUC1 (expressed in pancreatic and breast cancers); CD10 (previously known as common acute lymphoblastic leukemia antigen, or CALLA) or surface immunoglobulin (expressed in B cell leukemias and lymphomas); the α chain of the IL-2 receptor, T cell receptor, CD45R, CD4+/CD8+ (expressed in T cell leukemias and lymphomas); prostatespecific antigen and prostatic acid-phosphatase (expressed in prostate carcinoma); GP 100, MelanA/Mart-1, tyrosinase, gp75/brown, BAGE, and S-100 (expressed in melanoma); cytokeratins (expressed in various carcinomas); and CD19, CD20, and CD37 (expressed in lymphoma).

Tumor-associated antigens also include altered glycolipid and glycoprotein antigens, such as neuraminic acid-containing glycosphingolipids (e.g., GM2 and GD2, expressed in melanomas and some brain tumors); blood group antigens, particularly T and sialylated Tn antigens, which can be aberrantly expressed in carcinomas; and mucins, such as CA-125 and CA-19-9 (expressed on ovarian carcinomas) or the underglycosylated MUC-1 (expressed on breast and pancreatic carcinomas).

"Antigens of infectious agents" include components of protozoa, bacteria, fungi (both unicellular and multicellular), viruses, prions, intracellular parasites, helminths, and other infectious agents that can induce an immune response.

Bacterial antigens include antigens of gram-positive cocci, gram positive bacilli, gram-negative bacteria, anaerobic bacteria, such as organisms of the families Actinomycetaceae, Bacillaceae, Bartonellaceae, Bordetellae, Captophagaceae, Corynebacteriaceae, Enterobacteriaceae, Legionellaceae, Micrococcaceae, Mycobacteriaceae, Nocardiaceae, Pasteurellaccae, Pseudomonadaceae, Spirochaetaceae, Vibrionaceae and organisms of the genera *Acinetobacter, Brucella, Campylobacter, Erysipelothrix, Ewingella, Francisella, Gardnerella, Helicobacter, Levinea, Listeria, Streptobacillus* and *Tropheryma*.

Antigens of protozoan infectious agents include antigens of malarial plasmodia, *Leishmania* species, *Trypanosoma* species and *Schistosoma* species.

Fungal antigens include antigens of *Aspergillus, Blastomyces, Candida, Coccidioides, Cryptococcus, Histoplasma, Paracoccicioides, Sporothrix*, organisms of the order Mucorales, organisms inducing choromycosis and mycetoma and organisms of the genera *Trichophyton, Microsporum, Epidermophyton*, and *Malassezia*.

Viral peptide antigens include, but are not limited to, those of adenovirus, herpes simplex virus, papilloma virus, respiratory syncytial virus, poxviruses, HIV, influenza viruses, and CMV. Particularly useful viral peptide antigens include HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like.

Antigens, including antigenic peptides, can be bound to an antigen binding cleft of an antigen presenting complex either actively or passively, as described in U.S. Pat. No. 6,268,411, which is hereby incorporated by reference in its entirety. Optionally, an antigenic peptide can be covalently bound to a peptide binding cleft.

If desired, a peptide tether can be used to link an antigenic peptide to a peptide binding cleft. For example, crystallographic analyses of multiple class I MHC molecules indicate that the amino terminus of β2M is very close, approximately 20.5 Angstroms away, from the carboxyl terminus of an antigenic peptide resident in the MHC peptide binding cleft. Thus, using a relatively short linker sequence, approximately 13 amino acids in length, one can tether a peptide to the amino terminus of β2M. If the sequence is appropriate, that peptide will bind to the MHC binding groove (see U.S. Pat. No. 6,268,411).

Antigen-specific T cells which are bound to the aAPCs can be separated from cells which are not bound using magnetic enrichment, or other cell sorting or capture technique. Other processes that can be used for this purpose include flow cytometry and other chromatographic means (e.g., involving immobilization of the antigen-presenting complex or other ligand described herein). In one embodiment antigen-specific T cells are isolated (or enriched) by incubation with beads, for example, antigen-presenting complex/anti-CD28-conjugated paramagnetic beads (such as DYNABEADS®), for a time period sufficient for positive selection of the desired antigen-specific T cells.

In some embodiments, a population of T cells can be substantially depleted of previously active T cells using, e.g., an antibody to CD44, leaving a population enriched for naïve T cells. Binding nano-aAPCs to this population would not substantially activate the naïve T cells, but would permit their purification.

In still other embodiments, ligands that target NK cells, NKT cells, or B cells (or other immune effector cells), can be incorporated into a paramagnetic nanoparticle, and used to magnetically enrich for these cell populations, optionally with expansion in culture as described below. Additional immune effector cell ligands are described in PCT/US2014/25889, which is hereby incorporated by reference in its entirety.

Without wishing to be bound by theory, removal of unwanted cells may reduce competition for cytokines and growth signals, remove suppressive cells, or may simply provide more physical space for expansion of the cells of interest.

Enriched T cells are then expanded in culture within the proximity of a magnet to produce a magnetic field, which enhances T cell receptor clustering of aAPC bound cells. Cultures can be stimulated for variable amounts of time (e.g., about 0.5, 2, 6, 12, 36, 48, or 72 hours as well as continuous stimulation) with nano-aAPC. The effect of stimulation time in highly enriched antigen-specific T cell cultures can be assessed. Antigen-specific T cell can be placed back in culture and analyzed for cell growth, proliferation rates, various effector functions, and the like, as is known in the art. Such conditions may vary depending on the antigen-specific T cell response desired. In some embodiments, T cells are expanded in culture from about 2 days to about 3 weeks, or in some embodiments, about 5 days to about 2 weeks, or about 5 days to about 10 days. In some embodiments, the T cells are expanded in culture for about 1 week, after which time a second enrichment and expansion step is optionally performed. In some embodiments, 2, 3, 4, or 5 enrichment and expansion rounds are performed.

After the one or more rounds of enrichment and expansion, the antigen-specific T cell component of the sample will be at least about 1% of the cells, or in some embodiments, at least about 5%, at least about 10%, at least about 15%, or at least about 20%, or at least about 25% of the cells in the sample. Further, these T cells generally display an activated state. From the original sample isolated from the patient, the antigen-specific T cells in various embodiments are expanded from about 100-fold to about 10,000 fold, such as at least about 1000-fold, at least about 2000-fold, at least about 3,000 fold, at least about 4,000-fold, or at least about 5,000-fold in various embodiments. After the one or more rounds of enrichment and expansion, at least about $10^6$, or at least about $10^7$, or at least about $10^8$, or at least about $10^9$ antigen-specific T cells are obtained.

The effect of nano-aAPC on expansion, activation and differentiation of T cell precursors can be assayed in any number of ways known to those of skill in the art. A rapid determination of function can be achieved using a proliferation assay, by determining the increase of CTL, helper T cells, or regulatory T cells in a culture by detecting markers specific to each type of T cell. Such markers are known in the art. CTL can be detected by assaying for cytokine production or for cytolytic activity using chromium release assays.

In addition to generating antigen-specific T cells with appropriate effector functions, another parameter for antigen-specific T cell efficacy is expression of homing receptors that allow the T cells to traffic to sites of pathology (Sallusto et al., Nature 401, 708-12, 1999; Lanzavecchia & Sallusto, Science 290, 92-97, 2000).

For example, effector CTL efficacy has been linked to the following phenotype of homing receptors, CD62L+, CD45RO+, and CCR7−. Thus, a nano-aAPC-induced and/or expanded CTL population can be characterized for expression of these homing receptors. Homing receptor expression is a complex trait linked to initial stimulation conditions. Presumably, this is controlled both by the co-stimulatory complexes as well as cytokine milieu. One important cytokine that has been implicated is IL-12 (Salio et al., 2001). As discussed below, nano-aAPC offer the potential to vary individually separate components (e.g., T cell effector molecules and antigen presenting complexes) to optimize biological outcome parameters. Optionally, cytokines such as IL-12 can be included in the initial induction cultures to affect honing receptor profiles in an antigen-specific T cell population.

Optionally, a cell population comprising antigen-specific T cells can continue to be incubated with either the same nano-aAPC or a second nano-aAPC for a period of time sufficient to form a second cell population comprising an increased number of antigen-specific T cells relative to the number of antigen-specific T cells in the first cell population. Typically, such incubations are carried out for 3-21 days, preferably 7-10 days.

Suitable incubation conditions (culture medium, temperature, etc.) include those used to culture T cells or T cell precursors, as well as those known in the art for inducing formation of antigen-specific T cells using DC or artificial antigen presenting cells. See, e.g., Latouche & Sadelain, Nature Biotechno. 18, 405-09, April 2000; Levine et al., J. Immunol. 159, 5921-30, 1997; Maus et al., Nature Biotechnol. 20, 143-48, February 2002. See also the specific examples, below.

To assess the magnitude of a proliferative signal, antigen-specific T cell populations can be labeled with CFSE and analyzed for the rate and number of cell divisions. T cells can be labeled with CFSE after one-two rounds of stimulation with nano-aAPC to which an antigen is bound. At that point, antigen-specific T cells should represent 2-10% of the total cell population. The antigen-specific T cells can be detected using antigen-specific staining so that the rate and number of divisions of antigen-specific T cells can be followed by CFSE loss. At varying times (for example, 12, 24, 36, 48, and 72 hours) after stimulation, the cells can be analyzed for both antigen presenting complex staining and CFSE. Stimulation with nano-aAPC to which an antigen has not been bound can be used to determine baseline levels of proliferation. Optionally, proliferation can be detected by monitoring incorporation of 3H-thymidine, as is known in the art.

Antigen-specific T cells obtained using nano-aAPC, can be administered to patients by any appropriate routes, including intravenous administration, intra-arterial administration, subcutaneous administration, intradermal administration, intralymphatic administration, and intratumoral administration. Patients include both human and veterinary patients.

Antigen-specific regulatory T cells can be used to achieve an immunosuppressive effect, for example, to treat or prevent graft versus host disease in transplant patients, or to treat or prevent autoimmune diseases, such as those listed above, or allergies. Uses of regulatory T cells are disclosed, for example, in US 2003/0049696, US 2002/0090724, US 2002/0090357, US 2002/0034500, and US 2003/0064067, which are hereby incorporated by reference in their entireties.

Antigen-specific T cells prepared according to these methods can be administered to patients in doses ranging from about $5-10 \times 10^6$ CTL/kg of body weight ($\sim 7 \times 10^8$ CTL/treatment) up to about $3.3 \times 10^9$ CTL/kg of body weight ($\sim 6 \times 10^9$ CTL/treatment) (Walter et al., New England Journal of Medicine 333, 1038-44, 1995; Yee et al., J Exp Med 192, 1637-44, 2000). In other embodiments, patients can receive about $10^3$, about $5 \times 10^3$, about $10^4$, about $5 \times 10^4$, about $10^5$, about $5 \times 10^5$, about $10^6$, about $5 \times 10^6$, about $10^7$, about $5 \times 10^7$, about $10^8$, about $5 \times 10^8$, about $10^9$, about $5 \times 10^9$, or about $10^{10}$ cells per dose administered intravenously. In still other embodiments, patients can receive intranodal injections of, e.g., about $8 \times 10^6$ or about $12 \times 10^6$ cells in a 200 µl bolus. Doses of nano-APC that are administered with cells include about $10^3$, about $5 \times 10^3$, about $10^4$, about $5 \times 10^4$, about $10^5$, about $5 \times 10^5$, about $10^6$, about $5 \times 10^6$, about $10^7$, about $5 \times 10^7$, about $10^8$, about $5 \times 10^8$, about $10^9$, about $5 \times 10^9$, or about $10^{10}$ nano-aAPC per dose.

In an exemplary embodiment, the enrichment and expansion process is performed repeatedly on the same sample derived from a patient. A population of T cells is enriched and activated on Day 0, followed by a suitable period of time (e.g., about 3-20 days) in culture. Subsequently, nano-aAPC can be used to again enrich and expand against the antigen of interest, further increasing population purity and providing additional stimulus for further T cell expansion. The mixture of nano-aAPC and enriched T cells may subsequently again be cultured in vitro for an appropriate period of time, or immediately re-infused into a patient for further expansion and therapeutic effect in vivo. Enrichment and expansion can be repeated any number of times until the desired expansion is achieved.

In some embodiments, a cocktail of nano-aAPC, each against a different antigen, can be used at once to enrich and expand antigen T cells against multiple antigens simultaneously. In this embodiment, a number of different nano-aAPC batches, each bearing a different MHC-peptide, would be combined and used to simultaneously enrich T cells against each of the antigens of interest. The resulting T cell pool would be enriched and activated against each of these antigens, and responses against multiple antigens could thus be cultured stimultaneously. These antigens could be related to a single therapeutic intervention; for example, multiple antigens present on a single tumor.

In some embodiments, the patient receives immunotherapy with one or more checkpoint inhibitors, prior to receiving the antigen-specific T cells by adoptive transfer, or prior to direct administration of aAPCs bearing neoantigens identified in vitro through genetic analysis of the patient's tumor. In various embodiments, the checkpoint inhibitor(s) target one or more of CTLA-4 or PD-1/PD-L1, which may include antibodies against such targets, such as monoclonal antibodies, or portions thereof, or humanized or fully human versions thereof. In some embodiments, the checkpoint inhibitor therapy comprises ipilimumab or Keytruda (pembrolizumab).

In some embodiments, the patient receives about 1 to 5 rounds of adoptive immunotherapy (e.g., one, two, three, four or five rounds). In some embodiments, each administration of adoptive immunotherapy is conducted simultaneously with, or after (e.g., from about 1 day to about 1 week after), a round of checkpoint inhibitor therapy. In some embodiments, adoptive immunotherapy is provided about 1 day, about 2 days, or about 3 days after checkpoint inhibitor therapy.

In still other embodiments, adoptive transfer or direct infusion of nano-aAPCs to the patient comprises, as a ligand on the bead, a ligand that targets one or more of CTLA-4 or PD-1/PD-L1. In these embodiments, the method can avoid certain side effects of administering soluble checkpoint inhibitor therapy.

Methods for Personalized Therapy

In some aspects, the invention provides methods for personalized cancer immunotherapy. The methods are accomplished using the aAPCs to identify antigens to which the patient will respond, followed by administration of the appropriate peptide-loaded aAPC to the patient, or followed by enrichment and expansion of the antigen specific T cells ex vivo.

Genome-wide sequencing has dramatically altered our understanding of cancer biology. Sequencing of cancers has yielded important data regarding the molecular processes involved in the development of many human cancers. Driving mutations have been identified in key genes involved in pathways regulating three main cellular processes (1) cell fate, (2) cell survival and (3) genome maintenance. Vogelstein et al., *Science* 339, 1546-58 (2013).

Genome-wide sequencing also has the potential to revolutionize our approach to cancer immunotherapy. Sequencing data can provide information about both shared as well as personalized targets for cancer immunotherapy. In principle, mutant proteins are foreign to the immune system and are putative tumor-specific antigens. Indeed, sequencing efforts have defined hundred if not thousands of potentially relevant immune targets. Limited studies have shown that T cell responses against these neo-epitopes can be found in cancer patients or induced by cancer vaccines. However, the frequency of such responses against a particular cancer and the extent to which such responses are shared between patients are not well known. One of the main reasons for our limited understanding of tumor-specific immune responses is that current approaches for validating potential immunologically relevant targets are cumbersome and time consuming.

Thus, in some aspects, the invention provides a high-throughput platform-based approach for detection of T cell responses against neo-antigens in cancer. This approach uses the aAPC platform described herein for the detection of even low-frequency T cell responses against cancer antigens. Understanding the frequency and between-person variability of such responses would have important implications for the design of cancer vaccines and personalized cancer immunotherapy.

Although central tolerance abrogates T cell responses against self-proteins, oncogenic mutations induce neo-epitopes against which T cell responses can form. Mutation catalogues derived from whole exome sequencing provide a starting point for identifying such neo-epitopes. Using HLA binding prediction algorithms (Srivastava, *PLoS One* 4, e6094 (2009), it has been predicted that each cancer can have up 7-10 neo-epitopes. A similar approach estimated hundreds of tumor neo-epitopes. Such algorithms, however, may have low accuracy in predicting T cell responses, and only 10% of predicted HLA-binding epitopes are expected to bind in the context of HLA (Lundegaard C, *Immunology* 130, 309-18 (2010)). Thus, predicted epitopes must be validated for the existence of T cell responses against those potential neo-epitopes.

In certain embodiments, the nano-aAPC system is used to screen for neo-epitopes that induce a T cell response in a variety of cancers, or in a particular patient's cancer. Cancers may be genetically analyzed, for example, by whole exome-sequencing. For example, of a panel of 24 advanced adenocarcinomas, an average of about 50 mutations per tumor were identified. Of approximately 20,000 genes analyzed, 1327 had at least one mutation, and 148 had two or more mutations. 974 missense mutations were identified, with a small additional number of deletions and insertions.

A list of candidate peptides can be generated from overlapping nine amino acid windows in mutated proteins. All nine-AA windows that contain a mutated amino acid, and 2 non-mutated "controls" from each protein will be selected. These candidate peptides will be assessed computationally for MHC binding using a consensus of MHC binding prediction algorithms, including NetMHC and stabilized matrix method (SMM). Nano-aAPC and MHC binding algorithms have been developed primarily for HLA-A2 allele. The sensitivity cut-off of the consensus prediction can be adjusted until a tractable number of mutation containing peptides (~500) and non-mutated control peptides (~50) are identified.

A peptide library is then synthesized. MHC (e.g., A2) bearing aAPC are deposited in multi well plates and passively loaded with peptide. CD8 T cells may be isolated from PBMC of both A2 positive healthy donors and A2 positive pancreatic cancers patients (or other cancer or disease described herein). Subsequently, the isolated T cells are incubated with the loaded aAPCs in the plates for the enrichment step. Following the incubation, the plates are placed on a magnetic field and the supernatant containing irrelevant T cells not bound to the aAPCs is removed. The remaining T cells that are bound to the aAPCs will be cultured and allowed to expand for 7 to 21 days. Antigen specific expansion is assessed by re-stimulation with aAPC and intracellular IFNγ fluorescent staining.

In some embodiments, a patient's T cells are screened against an array or library of nanoAPCs, and the results are used for diagnostic or prognostic purposes. For example, the number and identity of T cell anti-tumor responses against mutated proteins, overexpressed proteins, and/or other tumor-associated antigens can be used as a biomarker to stratify risk. For example, the number of such T cell responses may be inversely proportionate to the risk of disease progression or risk of resistance or non-responsiveness to chemotherapy. In other embodiments, the patient's T cells are screened against an array or library of nano-APCs, and the presence of T cells responses, or the number or intensity of these T cells responses identifies that the patient has a sub-clinical tumor, and/or provides an initial understanding of the tumor biology.

In some embodiments, a patient or subject's T cells are screened against an array or library of paramagnetic aAPCs, each presenting a different candidate peptide antigen. This screen can provide a wealth of information concerning the subject or patient's T cell repertoire, and the results are useful for diagnostic or prognostic purposes. For example, the number and identity of T cell anti-tumor responses against mutated proteins, overexpressed proteins, and/or other tumor-associated antigens can be used as a biomarker to stratify risk, to monitor efficacy of immunotherapy, or predict outcome of immunotherapy treatment. Further, the number or intensity of such T cell responses may be inversely proportionate to the risk of disease progression or may be predictive of resistance or non-responsiveness to chemotherapy. In other embodiments, a subject's or patient's T cells are screened against an array or library of nano-APCs each presenting a candidate peptide antigen, and the presence of T cells responses, or the number or intensity of these T cells responses, provides information concerning the health of the patient, for example, by identifying autoimmune disease, or identifying that the patient has a sub-clinical tumor. In these embodiments, the process not only identifies a potential disease state, but provides an initial understanding of the disease biology.

Reagents/Kits

In another aspect of the invention, nano-aAPC can be provided in kits together with components for performing the enrichment and expansion process. Suitable containers for nano-aAPC include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle). Optionally, one or more different antigens can be bound to the nano-aAPC or can be supplied separately. Kits may comprise, alternatively or in addition, one or more multiwall plates or culture plates for T cells. In some embodiments, kits comprise a sealed container comprising aAPCS, a magnet, and optionally test tubes and/or solution or buffers for performing magnetic enrichment.

A kit can further comprise a second container comprising a pharmaceutically acceptable buffer, such as phosphate-buffered saline, Ringer's solution, or dextrose solution. It can also contain other materials useful to an end user, including other buffers, diluents, filters, needles, and syringes.

Kits also may contain reagents for assessing the extent and efficacy of antigen-specific T cell activation or expansion, such as antibodies against specific marker proteins, MHC class I or class II molecular complexes, TCR molecular complexes, anticlonotypic antibodies, and the like.

A kit can also comprise a package insert containing written instructions for methods of inducing antigen-specific T cells, expanding antigen-specific T cells, using nanoaAPC in the kit in various protocols. The package insert can be an unapproved draft package insert or can be a package insert approved by the Food and Drug Administration (FDA) or other regulatory body.

EXAMPLES

Example 1

Adoptive T cell therapy can mediate durable regression of cancer. To rapidly generate large numbers of functional tumor-specific T cells from naïve T cells, we developed an Enrichment+Expansion strategy using paramagnetic, nanoscale artificial Antigen Presenting Cells, capable of enriching rare tumor-specific T cells in a magnetic column while simultaneously activating them. Enrichment+Expansion resulted in greater than 1000-fold expansion of mouse and human tumor-specific T cells, and mice treated with tumor-specific CTL generated by Enrichment+Expansion had significantly less tumor growth. Streamlining the generation of large numbers of tumor-specific T cells in a cost effective, reproducible fashion through Enrichment+Expansion could be a powerful addition to autologous tumor immunotherapy protocols.

Adoptive transfer of tumor-specific T cells can mediate durable regression of cancer[1]. While pre-existing anti-tumor responses can only be cultured from a minority of cancer patients[2], T cells specific for a wide variety of tumor antigens can be generated by stimulation of naive precursor cells with tumor antigen[3]. This culture process relies on autologous antigen presenting cells and feeder cells, which are complex biologics that must be generated for each individual patient[4], significantly increasing the cost and complexity of adoptive immunotherapy.

Expansion of tumor-specific T cells is further complicated by the rarity of tumor-specific naive precursors, as few as one per million[5-7]. To generate the large numbers of tumor-specific T cells required for effective therapy[8-10], lymphocytes are repeatedly stimulated with antigen over many weeks, often followed by T cell selection and sub-cloning[11]. This labor-intensive process increases both the total number and antigen-specific frequency (or "purity") of tumor-specific T cells in the final cell product. Antigen-specific frequency is an independently important parameter for optimal expansion after transfer, since competition for growth signals from irrelevant, co-transferred cells significantly attenuates homeostatic expansion of anti-tumor T cells of interest[12-14].

Thus, there is a need for technologies that can quickly generate large numbers and high frequencies of tumor-specific T cells from naive precursors, without the added expense and complexity of cellular APC or feeder cells. The invention therefore provides a T cell enrichment and expansion strategy using nanoscale artificial Antigen Presenting Cells (nano-aAPC). The nano-aAPC exemplified here are paramagnetic iron-dextran nanoparticles, 50-100 nm in diameter, functionalized with two activating signals delivered by endogenous APC: signal 1, a cognate antigenic peptide presented in the context of MHC that binds the TCR; and signal 2, one of a number of co-stimulatory receptors that modulate T cell responses and promote effective activation (FIG. 1, top). Paramagnetic nano-aAPC are thus capable of both capturing cognate T cells in a magnetic enrichment column, and inducing antigen-specific T cell expansion (FIG. 1, bottom).

Figures 2A, 2B, 2C:
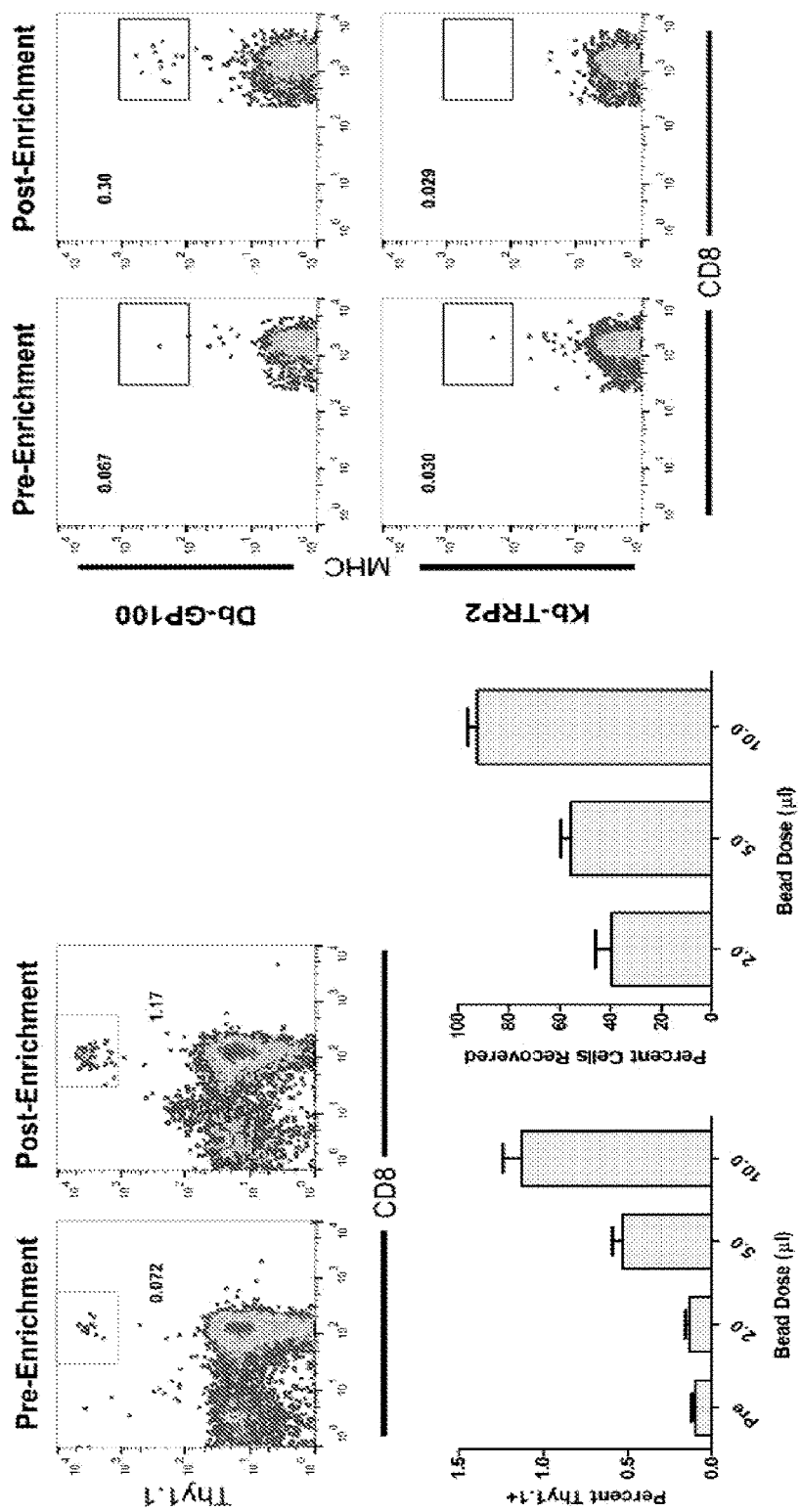
FIGS. 2A-2C. Nano-aAPC-Mediated Enrichment of Antigen-Specific T Cells.

Enrichment with nano-aAPC is performed by incubating naive, polyclonal mouse CD8+ T lymphocytes with nano-aAPC, passing the cell-particle mixture through a magnetic column, eluting and then culturing the magnet-bound fraction (FIG. 1). To assess efficacy of enrichment, a known number of Thy1.1+ pmel TCR transgenic T cells specific for Db-gp100 melanoma antigen were mixed at a 1:1000 ratio with Thy1.2+ CD8 T cells from B6 mice. After enrichment with pmel gp100-specific aAPC, the frequency of antigen-specific pmel T cells increased more than 10-fold from 0.07% before enrichment to 1.17% after enrichment in a dose-dependent manner (FIG. 2A). Optimizing the amount of nano-aAPC incubated with T cells increased the enrichment efficiency and resulted in recovery of up 95% of the added pmel T cells (FIG. 2B).

Enrichment of wild-type Db-gp100 cells from endogenous B6 CD8+ splenocytes was assessed by staining with soluble MHC pentamer. Db-gp100 specific frequency was below detectable levels prior to enrichment, but increased to 0.30% afterward. The frequency of non-specific Kb-Trp2 cells incubated with Db-gp100 particles did not increase (FIG. 2C).

After enrichment, magnet-bound fractions (positive fraction) of enriched cells and nano-aAPC were eluted and cultured in vitro. To study the effect of enrichment on subsequent proliferation, theenrichment procedure was "undone" in control samples by collecting the negative fraction (CD8+ T cells not bound to nano-aAPC), and adding it back to the positive fraction (FIG. 3A).

Enrichment significantly enhanced antigen-specific frequency and total T cell number after expansion. Seven days after enrichment with a Kb-Trp2 nano-aAPC, 17.6% of cells expanded from the positive fraction were Kb-Trp2 specific, compared to 1.46% of cells from the negative+positive, not enriched group (FIG. 3B). The enrichment procedure resulted in a 2-3 fold increase in total antigen-specific cells, despite greater numbers of total cells in the negative+ positive fraction. We hypothesize the increase in total T cell expansion may be mediated by reduced competition for lymphotrophic cytokines.

Figures 3A, 3B, 3C, 3D, 3E, 3F, 3G:
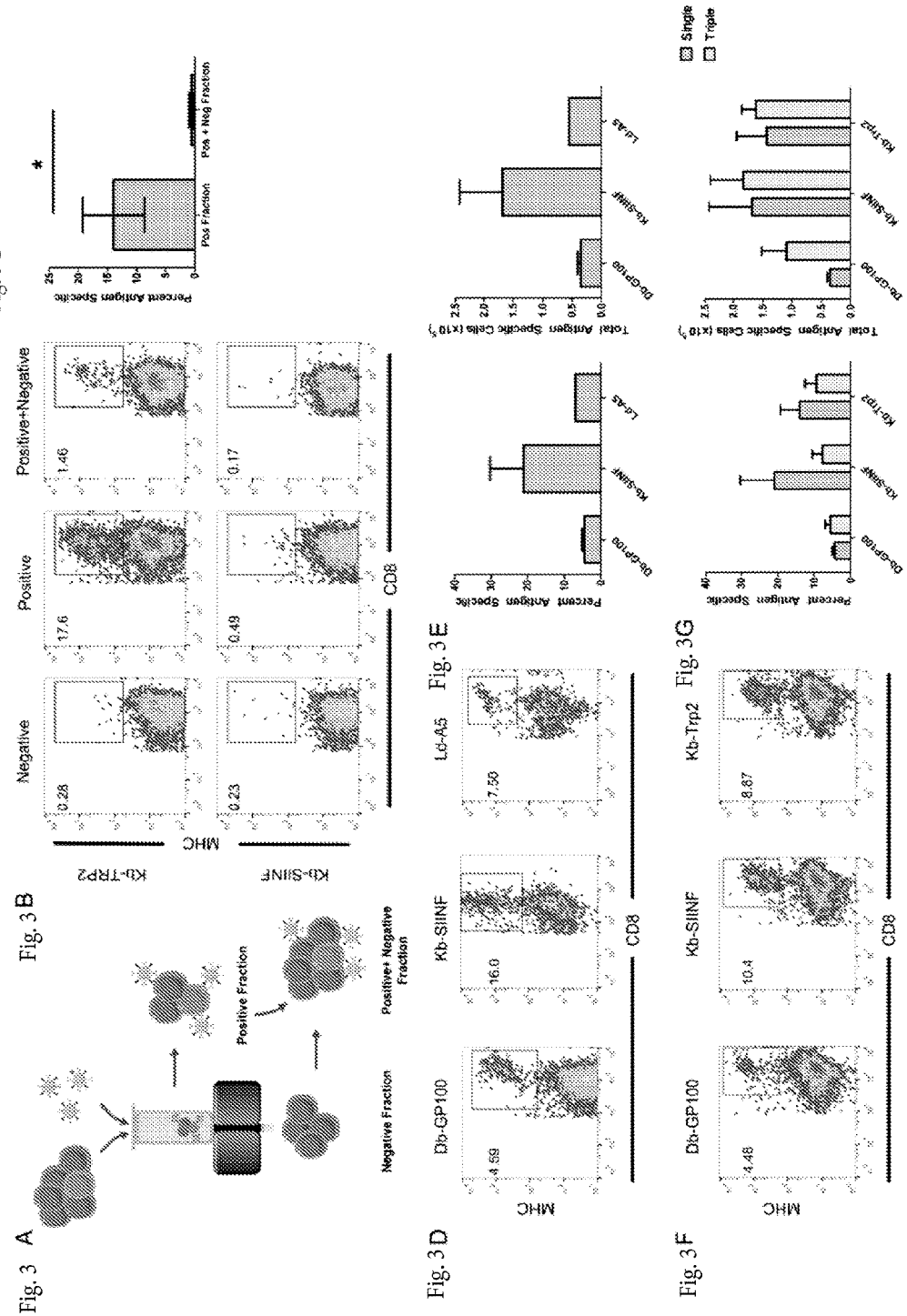
FIGS. 3A-3G. Expansion of Antigen-Specific T cells After Enrichment.

The Enrichment+Expansion approach was broadly applicable to a variety of tumor and model T cell antigens, including melanoma antigen gp100 (Db-gp100), the Kb-restricted ovalbumin antigen SIIN (Kb-SIIN), and the colon carcinoma antigen Ld-AH1/A5 (Ld-A5) (FIGS. 3D, 3E). Absolute numbers of antigen-specific cells and frequencies were antigen-dependent. Kb-SIIN responses consistently resulted in 20% antigen-specific cells after one week, whereas Db-gp100 specificities were approximately 5% and Ld-A5 approximately 7.5% of total T cells.

T cell proliferation was estimated from known precursor frequencies for the antigens of interest (Table 1). Precursor frequencies for CD8 responses to foreign antigens range from 10 s-100 s110[7,7] and are expected to be at the lower end of this range for the self-antigens such as Trp2. Precursor frequencies for Db-gp100 have been measured at 10 in 10[7,5] and 40-350 in $10^7$ for Kb-SIINF. After one week, 150,000 Trp2-specific cells were generated from $10^7$ polyclonal CD8 T cells; thus, we estimate Trp2-specific proliferation is between 100-1000 fold. In comparison, approximately 35,000 Db-gp100 and 150,000 Kb-SIINF specific T cells were generated from $10^7$ T cells, indicating up to 5,000 fold expansion for each antigen. This is comparable to the robust expansion observed after viral infection in vivo[18].

To validate these estimates, we labeled naive T cell populations with the proliferation marker dye CFSE, which is diluted in half with every round of T cell division. Four days following E+E, Kb-Trp2 tetramer binding T cells had diluted their CFSE below detectable limits. Transgenic pmel T cells stimulated with a moderate dose of nano-aAPC were used for comparison; these cells showed multiple peaks of CFSE fluorescence, indicating between 2-7 rounds of division. This allowed us to determine that enriched+expanded Trp2-specific T cells had completed more than 7 rounds of division, consistent with greater than 256-fold expansion after only four days. Expanded T cells showed a CD62L low CD44 high effector memory phenotype, consistent with robust activation and proliferation.

T cell expansion by E+E was compared to expansion using mature, bone marrow derived dendritic cells pulsed with Trp2 peptide. Stimulation of ten million naive lymphocytes resulted in $2\pm0.5\times10^4$ Trp2-specific T cells, with antigen-specific frequencies between 0.5-2.85%, approximately 10-fold lower in number and frequency than that achieved with E+E. This is consistent with expansion by APC and artificial APC in humans, where antigen-specific responses after one week of stimulation are frequently not detectable[19].

Simultaneous generation of T cell responses to multiple tumor antigens would increase the number of anti-tumor T cells generated from a single naive T cell population, and reduce the likelihood of tumor immune escape due to down-regulation of a single antigen[20-22]. We therefore developed a single-step E+E protocol for generating multiple anti-tumor populations simultaneously.

Naive lymphocytes were incubated with nano-aAPC bearing Db-gp100, Kb-SIINF, and Kb-Trp2 MHC dimers, each at the standard single-antigen dose. One week after "triple" E+E, antigen-specific T cells were detected by pentamer staining against each antigen of interest (FIG. 3F). While the frequency of each population was lower than that found in control samples stimulated with only one antigen (FIG. 3(i), the total antigen-specific cells was the same whether isolated individually or simultaneously (p>0.4 by two-way ANOVA) (FIG. 3G). Thus, the triple E+E protocol was as efficient for each tumor specific T cell population as any of the single-antigen controls.

Adoptively transferred tumor-specific T cells compete with co-transferred, non-tumor specific bystander cells for growth signals[12-14]. However, this effect has not been demonstrated for antigen-specific expansion of T cells that have been previously activated in vitro, as occurs during Enrichment+Expansion.

We thus combined tumor-specific pmel T cells and polyclonal, wild-type B6 cells in ratios that approximate the antigen specific frequencies achieved with and without E+E (10% and 1%, respectively). In each group, the total number of pmel T cells administered was the same ($10^5$); only the amount of bystander T cells differed ($10^6$ or $10^7$). The largest number and highest frequency of pmel T cells were observed in mice receiving fewer ($10^6$) bystander cells (FIG. 4A-B). Approximately $5.5 \pm 1.5 \times 10^5$ pmel T cells were recovered from the spleen and lymph nodes of these animals (FIG. 4B). Only $1.4 \pm 0.7 \times 10^5$ pmel T cells were recovered from animals receiving $10^7$ bystander cells ($p<0.05$ by two-way ANOVA with Tukey post-test). Thus, removal of competition from co-transferred cells enhanced engraftment and expansion after transfer.

In addition, tumor-specific T cells compete with host cells for growth signals[24], which has motivated the use of host radio- and chemo-based lymphodepletion prior to adoptive transfer[25,26]. Thus, animals receiving $10^6$ or $10^7$ bystander cells were either irradiated with 500 cGy gamma radiation 24 hours prior to transfer or left untreated, generating four experimental groups. Animals that were not irradiated showed poor engraftment, with less than $0.3 \times 10^5$ pmel T cells recovered in either the $10^6$ or $10^7$ bystander group (FIG. 4A-B). Thus, removal of both transferred bystander lymphocytes and/or host lymphocytes significantly increased the yield of adoptively transferred tumor-specific T cells in the host.

We next determined that tumor-specific lymphocytes generated by Enrichment+Expansion with nano-aAPC mediated rejection of established melanoma. B16-F10 cells, an aggressive, poorly immunogenic melanoma model, were implanted subcutaneously into B6 host mice and allowed to grow for eight days until tumors were palpable. In parallel, CD8 lymphocytes were isolated from naive B6 donor mice and Enriched+Expanded against Db-GP100 and Kb-Trp2 antigens, then transferred into hosts one day after lymphodepletion.

Animals receiving tumor-specific E+E donor lymphocytes had significantly less tumor growth than untreated mice, or mice receiving equivalent numbers of lymphocytes generated against irrelevant Kb-SIINF antigen (FIG. 4C). Eighteen days after tumor injection, mean tumor area for untreated mice was $130 \pm 12$ mm$^2$, compared to $144 \pm 11$ mm$^2$ for Kb-SIINF treated mice and $22 \pm 9$ mm$^2$ for Db-gp100/Kb-Trp2 treated mice ($p<0.05$ by ANOVA with Tukey post-test).

All mice in untreated and Kb-SIINF treated groups were sacrificed by day 22 due to excessive tumor burden. By comparison, no mice in the Db-gp100/Kb-Trp2 group were sacrificed until day 24, and 2/8 mice had no detectable tumor 2 months after implantation ($p<0.01$ by Mantel-Cox). Median survival was significantly greater in the E+E treated group (28 days) than the untreated (20 days) or non-cognate treated (20 days) group. Thus, E+E lymphocytes cultured from naive cells for only a week were able to delay and in some cases completely reject established B16 melanoma.

Figures 5A, 5B:
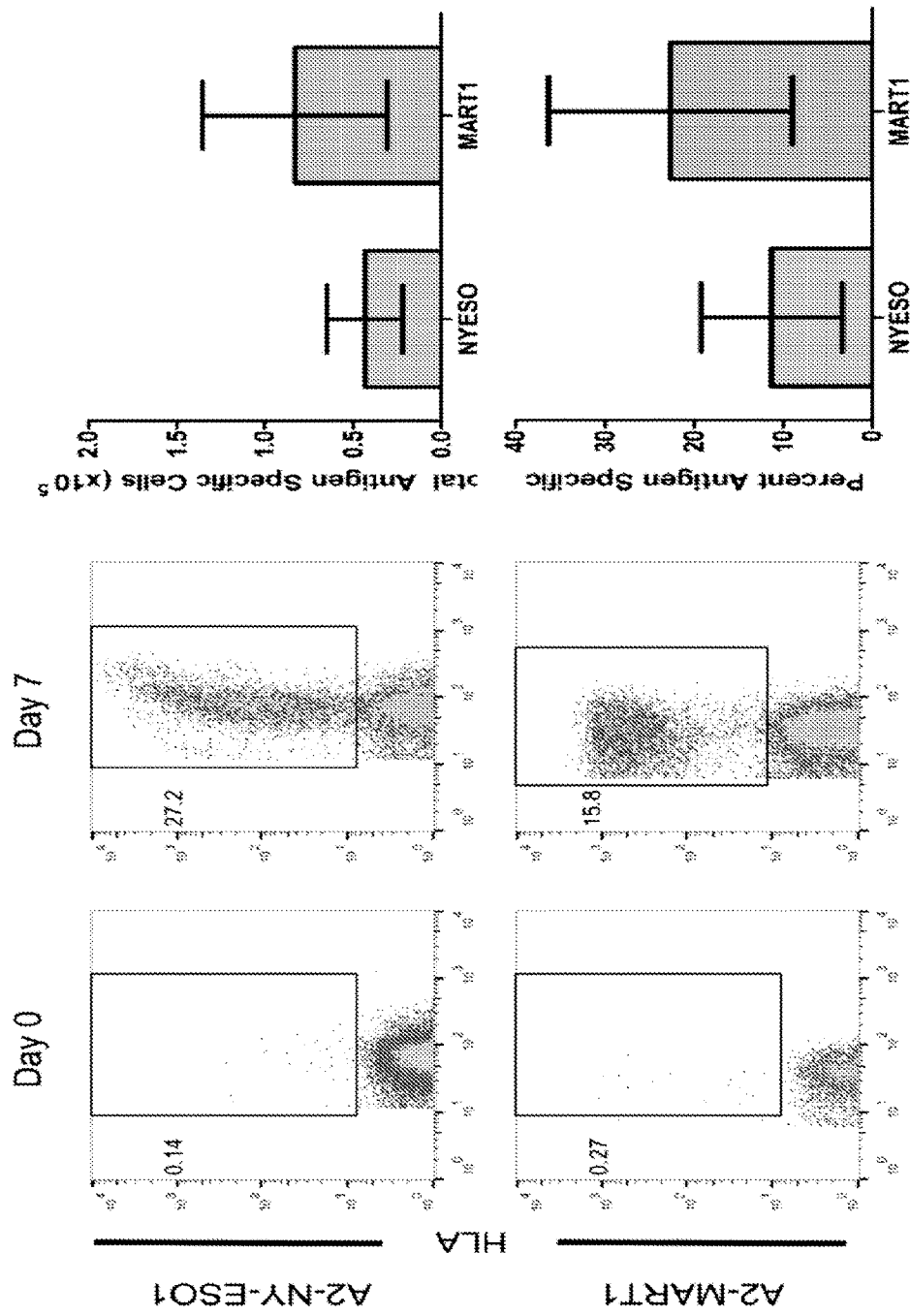
FIGS. 5A-5B: Expansion of Human Anti-Tumor Response. CD8+ PBMCs were isolated from healthy donors and expanded using the enrichment and expansion protocol for one week.

Enrichment+Expansion by nano-aAPC functionalized with HLA-A2 is also effective at expanding human anti-tumor responses from naive lymphocytes. Human CD8+ lymphocytes were isolated from peripheral blood mononuclear cells of healthy donors, and E+E was performed with nano-aAPC bearing either NY-ESO1 or MART1 tumor antigens. After one week, $44,000 \pm 21,000$ NY-ESO1 specific cells were generated, representing approximately 1000-fold precursor expansion (Table 1, FIG. 5). For MART1 responses, $83,000 \pm 37,000$ were generated in one week; this represents approximately 100-fold expansion, reflecting the high precursor frequency of MART1 responses found even in healthy donors 27 (Table 1, FIG. 5). Thus Enrichment+Expansion is not limited to murine T cells, but is also a robust approach for the expansion of naïve, low frequency, anti-tumor human CTL.

Wide-spread application of adoptive immunotherapy for cancer is limited by the availability of cost-effective and convenient sources of tumor-specific cells. Here, we developed a streamlined technology for quickly expanding large numbers of high frequency tumor-specific lymphocytes from naive cells, with more than 1000-fold expansion in one week. We further demonstrate that removing irrelevant bystander cells by enrichment confers a significant survival and proliferation advantage to tumor-specific T cells both during in vitro culture and after adoptive transfer in vivo.

While antigen-specific T cells can be enriched using MHC tetramers after T cell expansion[28-30], our platform simplifies this process by allowing enrichment and expansion to be performed with a single reagent. Furthermore, cross-linking of TCR by multimeric MHC in the absence of co-stimulation can induce T cell apoptosis or anergy[31-33] with deletion of up to one-half of antigen-specific cells after tetramer engagement. Thus, the use of a single platform for both T cell enrichment and expansion simplifies and improves on existing protocols.

Tumor-specific T cells can now be generated by genetic engineering of lymphocytes to express anti-cancer TCR or chimeric antigen receptors (CAR)[1] and are a promising approach to increasing availability; however, the use of foreign receptors that have not been modulated by endogenous tolerance mechanisms theoretically increases the likelihood of cross-reactivity and toxicity, with significant toxicities observed in trials[34]. Autologous melanoma-infiltrating lymphocytes have proven highly effective in clinical trials, but cannot be cultured from all melanoma patients or for most other cancers[2].

A reliable method for generating responses from endogenous, naive cells could thus increase both availability and safety[3]. Existing protocols have demonstrated encouraging results with responses derived from naive cells[35,36], but rely on repeated stimulation and cloning over many weeks to months to generate between $10^8$ and $10^{10}$ tumor-reactive T cells[36-38] administered per infusion, leading to high cost and complexity. E+E is a promising novel approach, both in terms of total number and purity, compared to existing attempts to generate robust expansion in a shorter period. For example, expansion of NY-ESO1 with dendritic cell-based approaches after one week in culture is either undetectable or not reported, making the achievement of antigen specific purities between 4-27% with 1000-fold expansion all the more remarkable. In contrast, several groups have reported effective expansion of the high precursor frequency MART1 response. For example, the novel DC-based ACE-CD8 platform described by Wolfl et al[39] is a well-characterized system that has been very useful in helping define and optimize requirements for expansion of human CD8 cells and shows an impressive 10 day expansion, suggesting that further optimization of culture conditions is required to support optimal MART1 expansion in vitro. Nevertheless, to generate the amount of T cells which may be needed clinically, the DC-based ACE-CD8 platform would still require potentially multiple plasmapherises from patients to generate weekly cultures of DC for expansion or use of non-antigen-specific techniques. Nano-aAPC based E+E is not subject to such constraints.

Assuming tumor-specific T cell precursor frequencies of approximately 1-10 per million, approximately $0.5 \times 10^{10}$ CD8 T cells harvested from a single leukapharesis, and 1000-5000 fold expansion observed with E+E, more than $10^8$ antigen specific T cells could be generated in one week. Simultaneously expanding multiple antigens would increase this number further, yielding sufficient cells for infusion. Thus, by eliminating the need to culture cellular APCs and streamlining the generation of large numbers of high-frequency tumor-specific T cells, Enrichment+Expansion can be a powerful addition to autologous tumor immunotherapy protocols.

Methods

Mice and Reagents.

Pmel TCR/Thy1a Rag-/- transgenic mice were maintained as homozygotes. C57BL/6j and Balb/C mice were purchased from Jackson Laboratories (Bar Harbor, Me.). All mice were maintained according to Johns Hopkins University's Institutional Review Board. Fluorescently labeled monoclonal antibodies were purchased from BioLegend (San Diego, Calif.).

Preparation of MHC-Ig Dimers and Nano-aAPC.

Soluble MHC-Ig dimers, Kb-Ig, Db-Ig, and A2-Ig were prepared and loaded with peptides as described.[19] Nano-aAPC were manufactured by direct conjugation of MHC-Ig dimer and anti-CD28 antibody (37.51; BioLegend) to MACS Microbeads (Miltenyi Biotec) as described.[15]

Lymphocyte Isolation.

Mouse lymphocytes were obtained from homogenized mouse spleens and lymph nodes followed by hypotonic lysis of RBC. Cytotoxic lymphocytes were isolated using a CD8 no-touch isolation kit and magnetic enrichment column from Miltenyi Biotec (Cologne, Germany) following the manufacture's protocol. Where applicable, cells were labeled with carboxyfluorescein succinimidyl ester (CFSE) for 15 minutes at 37° C., then washed extensively. For human studies, the ethical committee of the Johns Hopkins University approved this study and all healthy volunteers gave written informed consent. PBMC of HLA-A2+ donors were obtained by density gradient centrifugation (Lymphocyte Separation Medium Ficoll-Paque, GE Healthcare). Subsequently, CD8+ T cells were isolated using a CD8 no-touch isolation kit and magnetic enrichment column from Miltenyi Biotec (Cologne, Germany) following the manufacture's protocol. Purified CD8+ T cells were stained with nano-aAPC for 1 h at 4° C. and enriched magnetically utilizing MS-columns (Miltenyi Biotec).

Enrichment and Expansion.

10 million CD8-enriched lymphocytes were incubated with 10 µl of nano-aAPC for 1 hour at 4° C. Cell-particle mixtures were subsequently passed through a magnetic enrichment column, the negative fraction was collected and the positive fraction was eluted. Isolated fractions were mixed and cultured in 96 well round bottom plates for 7 days in complete RPMI-1640 medium supplemented with 10% human autologous serum and 3% T cell growth factor (TCGF) in 96-well round-bottom plates (Falcon) in a humidified incubator providing 5% $CO_2$ and 37° C. for 1 week. Medium and TCGF were replenished once a week. Specificity of CTL was monitored on day 0 and 7, by tetramer and MHC-Ig stain utilizing FACS analysis.

Bystander In Vivo Experiments.

Mixtures of pmel and wild-type B6 CD8+ T lymphocytes were mixed at the indicated ratios. Cell mixtures were cultured for one week with 20 µl of Db-gp100 nano-aAPC prior to adoptive transfer. Transient lymphopenia was induced in host mice by sublethal irradiation (500 cGy) one day before adoptive transfer with a MSD Nordion Gamma-cell dual Cs137 source (Johns Hopkins Molecular Imaging Center) in the indicated groups. Mice were treated both the day of and the day after adoptive transfer with 30,000 units intraperitoneal IL-2. Seven and twenty-days after adoptive transfer, three mice per group were sacrificed and lymphocytes were isolated from peripheral blood, spleen, and inguinal, cervical, and axillary lymph nodes, and then stained with anti-Thy1.1 antibody.

Tumor Rejection Experiments.

Tumor rejection experiments were performed as above, except $3 \times 10^5$ B16 melanoma cells were injected subcutaneously ten days prior to adoptive T cell transfer. Transient lymphopenia was induced one day before adoptive transfer as described above. 10 million naive lymphocytes from each donor were used to generate antigen-specific cells for each tumor host (up to 3 hosts per donor), representing approximately $2 \times 10^5$ tumor-specific T cells generated and transferred after one week of culture. Mice were treated both the day of and the day after adoptive transfer with 30,000 units intraperitoneal IL-2. Tumor growth was monitored at 2 day intervals using digital calipers. Mice were sacrificed once tumors reached 150 $mm^2$.

TABLE 1

Antigen-Specific T Cell Expansion. Estimated T cell precursor frequencies per 10 million lymphocytes. Antigen-specific cells generated from 10 million lymphocytes (with reference).

| Antigen | Precursor Frequency (per 10 million cells) | Ag-Specific Cells | Fold Expansion |
| --- | --- | --- | --- |
| Kb-Trp2 | 10-100[7] | 130,000 ± 80,000 | 1,300-13,000x |
| Db-gp100 | 10-100[5] | 35,000 ± 10,000 | 350-3,500x |
| Kb-SIINF | 20-350[7] | 150,000 ± 75,000 | 450-7,500x |
| A2-NY-ESO1 | 36[27] | 44,000 ± 21,000 | 1200x |
| A2-MART1 | 1000[27] | 83,000 ± 37,000 | 83x |

Example 2

Expansion of Neo-Antigens

The tumor antigens described thus far are previously known "shared antigens" derived from proteins that are over-expressed in tumors, and present on or shared between tumors from multiple patients. With the advent of genome-wide sequencing, it has been shown that most cancers contain clonal, non-synonymous single base pair substitutions that may bind to the patient's MHC, thereby opening up new avenues for immunotherapy.[29] Subsequent analyses have reinforced this idea.[38-45] These "neo-antigens" have theoretical advantages over shared antigens as tumor targets, such as greater specificity for tumor tissue and potentially higher-affinity TCR-MHC interactions. However, the pattern of mutation is unique in each cancer, and methods must be developed for rapid personalized identification and targeting of these neo-antigens.

To generate T cell responses against neo-antigens using Enrichment+Expansion, we utilized published "mutomes" described for the mouse melanoma line B16 and colon carcinoma line CT26.[46,47] Briefly, genomic and transciptomic data sets were combined to identify expressed single base pair substitutions (FIG. 6A). Eight or nine flanking amino acids upstream and downstream of each SBS were extracted in silico. These ~17-amino acid sequences were then processed by NetMHC, an algorithm that predicts binding of peptides to human HLA as well as mouse MHC alleles using an artificial neural network[48]. This algorithm predicted amino acid neo-epitopes 8 to 10 amino acids in length for CT26 and B16 (Table 2). Seven candidate peptides representing a wide range of predicted affinities, 2 from CT26 and 5 from B16, were synthesized and used to generate neo-epitope specific nano-aAPC. E+E with nano-aAPC bearing these neo-epitopes was then performed and evaluated with MHC multimers at Day 7.

Antigen-specific populations from Day 7 cultures were identified for both of the two CT26-derived candidate peptides tested (FPS and SAF). FIG. 6B shows representative Day 7 cognate MHC staining of Ld-FPS and Ld-SAF activated samples. Peptides derived from the B16 mutome showed responsive (Db-YTG) and non-responsive (Kb-LAY) staining patterns (FIG. 6B); overall 2/5 peptides explored (Db-YTG and Kb-VDW) showed strong responses, 2/5 showed moderate responses (Db-IAM and Db-RTF), and 1/5 was non-responsive (Kb-LAY). Peptide affinity for MHC as predicted by NetMHC (Table 2) did not accurately predict E+E response; strong responders YTG and VDW had low predicted affinities at 991 and 9066 nM respectively, whereas the non-responder LAY and equivocal responder IAM had high predicted affinities at 69 and 5 nM respectively. Overall, the total number of cells generated at Day 7 approximated those observed with the shared antigens Db-GP100 and Ld-A5, ranging from 15,000-40,000 (FIG. 6C), but was less than the shared antigens Kb-TRP2 and Kb-SIIN.

TABLE 2

Candidate Neo-Epitopes

| Best Proteins for Peptides (bold = 10 mer) | Mutant Peptide (includes 10 mers) | Predicted Affinity (nM) | Allele |
|---|---|---|---|
| Actn4 | VTFQAFIDV | 210 | H-2-Kb |
| Atp11a | QSLGFTYL | 19 | H-2-Kb |
| Cpsf31 | RTFANNPGPM | 2043 | H-2-Db |
| Dag1 | TTTTKKARV | 2024 | H-2-Kb |
| Ddb1 | VLMINGEEV | 153 | H-2-Db |
| Ddx23 | QTAMFTATM | 112 | H-2-Kb |
| Dpf2 | LALPNNYCDV | 318 | H-2-Db |
| Eef2 | ESFAFTADL | 277 | H-2-Kb |
| Fat1 | IAMQNTTQL | 5 | H-2-Db |
| Fzd7 | VAHVAAFL | 87 | H-2-Kb |
| Kif18b | VDWENVSPEL | 9066 | H-2-Kb |
| Mthfd1l | TILNCFHDV | 1761 | H-2-Kb |
| Orc2 | VVPSFSAEI | 39 | H-2-Kb |
| Pbk | AAVILRDAL | 121 | H-2-Db |
| Plod2 | VWQIFENPV | 111 | H-2-Kb |
| S100a132510039018 | TVVCTFFTF | 379 | H-2-Kb |
| Sema3b | VSAAQAERL | 1487 | H-2-Kb |
| Tm9sf3 | AIYHHASRAI | 191 | H-2-Kb |
| Tnpo3 | LAYLMKGL | 69 | H-2-Kb |
| Tubb3 | YTGEAMDEM | 991 | H-2-Db |
| Wdr82 | TNGSFIRLL | 87 | H-2-Kb |

List of candidate peptide sequences containing neo-epitopes derived from B16 tumors, including MHC affinity as predicted by NetMHC.

REFERENCES FOR EXAMPLE 2 ONLY (1) Restifo, N. P.; Dudley, M. E.; Rosenberg, S. a. Adoptive Immunotherapy for Cancer: Harnessing the T Cell Response. *Nat. Rev. Immunol.* 2012, 12, 269-281.

(2) Barrett, D. M.; Singh, N.; Porter, D. L.; Grupp, S. a; June, C. H. Chimeric Antigen Receptor Therapy for Cancer. *Annu. Rev. Med.* 2014, 65, 333-347.

(3) Kershaw, M. H.; Westwood, J. a; Darcy, P. K. Gene-Engineered T Cells for Cancer Therapy. *Nat. Rev. Cancer* 2013, 13, 525-541.

(4) Yee, C. The Use of Endogenous T Cells for Adoptive Transfer. *Immunol. Rev.* 2014, 257, 250-263.

(5) Morgan, R. A.; Chinnasamy, N.; Abate-daga, D.; Gros, A.; Robbins, P. F.; Zheng, Z.; Dudley, M. E.; Feldman, S. A.; Yang, J. C.; Sherry, R. M.; et al. Cancer Regression and Neurological Toxicity Following Anti-Mage-A3 TCR Gene Therapy. *J. Immunother.* 2013, 36, 133-151.

(6) Zhong, S.; Malecek, K. T-Cell Receptor Affinity and Avidity Defines Antitumor Response and Autoimmunity in T-Cell Immunotherapy. *Proc . . .* 2013, 110.

(7) Wherry, E. J. T Cell Exhaustion. *Nat. Immunol.* 2011, 131, 492-499.

(8) Rabinovich, G. a; Gabrilovich, D.; Sotomayor, E. M. Immunosuppressive Strategies That Are Mediated by Tumor Cells. *Anna. Rev. Immunol.* 2007, 25, 267-296.

(9) Dudley, M. E.; Rosenberg, S. a. Adoptive-Cell-Transfer Therapy for the Treatment of Patients with Cancer. *Nat. Rev. Cancer* 2003, 3, 666-675.

(10) Itzhaki, O.; Hovav, E.; Ziporen, Y.; Levy, D.; Kubi, A.; Zikich, D.; Hershkovitz, L.; Treves, A. J.; Shalmon, B.; Zippel, D.; et al. Establishment and Large-Scale Expansion of Minimally Adoptive Transfer Therapy. *J Immunother.* 2011, 34, 212-220.

(11) Satthaporn, S.; Robins, A.; Vassanasiri, W.; El-Sheemy, M.; Jibril, J. a; Clark, D.; Valerio, D.; Eremin, O. Dendritic Cells Are Dysfunctional in Patients with Operable Breast Cancer. *Cancer Immunol. Immunother.* 2004, 53, 510-518.

(12) Hurwitz, A. a; Watkins, S. K. Immune Suppression in the Tumor Microenvironment: A Role for Dendritic Cell-Mediated Tolerization of T Cells. *Cancer Immunol. Immunother.* 2012, 61, 289-293.

(13) Ma, Y.; Shurin, G. V; Gutkin, D. W.; Shurin, M. R. Tumor Associated Regulatory Dendritic Cells. *Semin. Cancer Biol.* 2012, 22, 298-306.

(14) Perica, K.; De Leon Medero, A.; Durai, M.; Chiu, Y. L.; Bicler, J. G.; Sibener, L.; Niemoller, M.; Assenmacher, M.; Richter, A.; Edidin, M.; et al. Nanoscale Artificial Antigen Presenting Cells for T Cell Immunotherapy. *Nanomedicine* 2013, 10, 119-129.

(15) Zhang, N.; Bevan, M. J. CD8(+) T Cells: Foot Soldiers of the Immune System. *Immunity* 2011, 35, 161-168.

(16) Fahmy, T. M.; Bieler, J. G.; Edidin, M.; Schneck, J. P. Increased TCR Avidity after T Cell Activation: A Mechanism for Sensing Low-Density Antigen. *Immunity* 2001, 14, 135-143.

(17) Perica, K.; Tu, A.; Richter, A.; Bieler, J. G.; Edidin, M.; Schneck, J. P. Magnetic Field-Induced T Cell Receptor Clustering by Nanoparticles Enhances T Cell Activation and Stimulates Antitumor Activity. *ACS Nano* 2014, 8, 2252-2260.

(18) He, C.; Hu, Y.; Yin, L.; Tang, C.; Yin, C. Effects of Particle Size and Surface Charge on Cellular Uptake and Biodistribution of Polymeric Nanoparticles. *Biomaterials* 2010, 31, 3657-3666.

(19) Decuzzi, P.; Godin, B.; Tanaka, T.; Lee, S.-Y.; Chiappini, C.; Liu, X.; Ferrari, M. Size and Shape Effects in the Biodistribution of Intravascularly Injected Particles. *J. Control. Release* 2010, 141, 320-327.

(20) Semete, B.; Booysen, L.; Lemmer, Y.; Kalombo, L.; Katata, L.; Verschoor, J.;
Swai, H. S. In Vivo Evaluation of the Biodistribution and Safety of PLGA Nanoparticles as Drug Delivery Systems. *Nanomedicine* 2010, 6, 662-671.

(21) Schamel, W. W. a; Alarcon, B. Organization of the Resting TCR in Nanoscale Oligomers. *Immunol. Rev.* 2013, 251, 13-20.

(22) Rizzuto, G. a; Merghoub, T.; Hirschhorn-Cymerman, D.; Liu, C.; Lesokhin, A. M.; Sahawneh, D.; Thong, H.; Panageas, K. S.; Perales, M.-A.; Altan-Bonnet, G.; et al. Self-Antigen-Specific CD8+ T Cell Precursor Frequency Determines the Quality of the Antitumor Immune Response. *J. Exp. Med.* 2009, 206, 849-866.

(23) Jenkins, M. K.; Chu, H. H.; McLachlan, J. B.; Moon, J. J. On the Composition of the Preimmune Repertoire of T Cells Specific for Peptide-Major Histocompatibility Complex Ligands. *Annu. Rev. Immunol.* 2010, 28, 275-294.

(24) Jenkins, M. K.; Moon, J. J. The Role of Naive T Cell Precursor Frequency and Recruitment in Dictating Immune Response Magnitude. *J. Immunol.* 2012, 188, 4135-4140.

(25) Chapuis, A.; Ragnarsson, G. Transferred WT1-Reactive CD8+ T Cells Can Mediate Antileukemic Activity and Persist in Post-Transplant Patients. *Sci. Transl. Med.* 2013, 5, 174ra27.

(26) Klebanoff, C. a; Gattinoni, L.; Palmer, D. C.; Muranski, P.; Ji, Y.; Hinrichs, C. S.; Borman, Z. a; Kerkar, S. P.; Scott, C. D.; Finkelstein, S. E.; et al. Determinants of Successful CD8+ T-Cell Adoptive Immunotherapy for Large Established Tumors in Mice. *Clin. Cancer Res.* 2011, 17, 5343-5352.

(27) Wen, F.; Thisted, R. A Systematic Analysis of Experimental Immunotherapies on Tumors Differing in Size and Duration of Growth . . . 2012, 172-178.

(28) Besser, M. J.; Shapira-Frommer, R.; Treves, A. J.; Zippel, D.; Itzhaki, 0.; Hershkovitz, L.; Levy, D.; Kubi, A.; Hovav, E.; Chermoshniuk, N.; et al. Clinical Responses in a Phase II Study Using Adoptive Transfer of Short-Term Cultured Tumor Infiltration Lymphocytes in Metastatic Melanoma Patients. *Clin. Cancer Res.* 2010, 16, 2646-2655.

(29) Segal, N. H.; Parsons, D. W.; Peggs, K. S.; Vciculescu, V.; Kinzler, K. W.; Vogelstein, B.; Allison, J. P. Epitope Landscape in Breast and Colorectal Cancer. *Cancer Res.* 2008, 68, 889-892.

(30) Smith-Garvin, J. E.; Koretzky, G. a; Jordan, M. S. T Cell Activation. *Annu. Rev. Immunol.* 2009, 27, 591-619.

(31) Durai, M.; Krueger, C.; Ye, Z.; Cheng, L.; Mackensen, A.; Oelke, M.; Schneck, J. P. In Vivo Functional Efficacy of Tumor-Specific T Cells Expanded Using IILA-Ig Based Artificial Antigen Presenting Cells (aAPC). *Cancer Immunol. Immunother.* 2009, 58, 209-220.

(32) Sarkar, S.; Teichgraber, V.; Kalia, V.; Polley, A.; Masopust, D.; Harrington, L. E.; Ahmed, R.; Wherry, E. J. Strength of Stimulus and Clonal Competition Impact the Rate of Memory CD8 T Cell Differentiation. *J. Immunol.* 2007, 179, 6704-6714.

(33) Oelke, M.; Kurokawa, T.; Ilentrich, I.; Behringer, D.; Cerundolo, V.; Lindemann, A. Functional Characterization of CD8 1 Antigen-Specific Cytotoxic T Lymphocytes after Enrichment Based on Cytokine Secretion: Comparison with the MHC-Tetramer Technology. 2000, 544-549.

(34) Oelke, M.; Maus, M. V; Didiano, D.; June, C. II.; Mackensen, A.; Schneck, J. P. Ex Vivo Induction and Expansion of Antigen-Specific Cytotoxic T Cells by HLA-Ig-Coated Artificial Antigen-Presenting Cells. *Nat. Med.* 2003, 9, 619-624.

(35) Seliger, B. Molecular Mechanisms of MHC Class I Abnormalities and APM Components in Human Tumors. *Cancer Immunol. Immunother.* 2008, 57, 1719-1726.

(36) Kaluza, K. M.; Thompson, J. M.; Kottke, T. J.; Flynn Gilmer, H. C.; Knutson, D. L.; Vile, R. G. Adoptive T Cell Therapy Promotes the Emergence of Genomically Altered Tumor Escape Variants. *Int. J. Cancer* 2012, 131, 844-854.

(37) Jensen, S. M.; Twitty, C. G.; Maston, L. D.; Antony, P. a; Lim, M.; Hu, H.-M.; Petrausch, U.; Restifo, N. P.; Fox, B. a. Increased Frequency of Suppressive Regulatory T Cells and T Cell-Mediated Antigen Loss Results in Murine Melanoma Recurrence. *J. Immunol.* 2012, 189, 767-776.

(38) Duan, F.; Duitama, J.; Al Seesi, S.; Ayres, C. M.; Corcelli, S. a.; Pawashe, a. P.; Blanchard, T.; McMahon, D.; Sidney, J.; Sette, a.; et al. Genomic and Bioinformatic Profiling of Mutational Neoepitopes Reveals New Rules to Predict Anticancer Immunogenicity. *J. Exp. Med.* 2014.

(39) Rajasagi, M.; Shukla, S. a; Fritsch, E. F.; Keskin, D. B.; DeLuca, D.; Carmona, E.; Zhang, W.; Sougnez, C.; Cibulskis, K.; Sidney, J.; et al. Systematic Identification of Personal Tumor-Specific Neoantigens in Chronic Lymphocytic Leukemia. *Blood* 2014, 124, 453-462.

(40) Fritsch, E. F.; Rajasagi, M.; Ott, P. a; Brusic, V.; Hacohen, N.; Wu, C. J. HLA-Binding Properties of Tumor Neoepitopes in Humans. *Cancer Immunol. Res.* 2014, 2, 522-529.

(41) Srivastava, P. K.; Duan, F. Harnessing the Antigenic Fingerprint of Each Individual Cancer for Immunotherapy of Human Cancer: Genomics Shows a New Way and Its Challenges. *Cancer Immunol. Immunother.* 2013, 62, 967-974.

(42) Tran, E.; Turcotte, S.; Gros, A.; Robbins, P. F.; Lu, Y.; Dudley, M. E.; Parkhurst, M. R.; Yang, J. C.; Rosenberg, S. A. Cancer Immunotherapy Based on Mutation-Specific CD4+ T Cells in a Patient with Epithelial Cancer. *Sci. Transl. Med.* 2014, 9, 641-645.

(43) Matsushita, H.; Vesely, M.; Koboldt, D. Cancer Exome Analysis Reveals a T-Cell-Dependent Mechanism of Cancer Immunoediting. *Nature* 2012, 482, 400-404.

(44) Yadav, M.; Jhunjhunwala, S.; Phung, Q. T.; Lupardus, P.; Tanguay, J.; Bumbaca, S.; Franci, C.; Cheung, T. K.; Fritsche, J.; Weinschenk, T.; et al. Predicting Immunogenic Tumour Mutations by Combining Mass Spectrometry and Exome Sequencing. *Nature* 2014, 515, 572-576.
(45) Gubin, M. M.; Zhang, X.; Schuster, H.; Caron, E.; Ward, J. P.; Noguchi, T.; Ivanova, Y.; Hundal, J.; Arthur, C. D.; Krebber, W.-J.; et al. Checkpoint Blockade Cancer Immunotherapy Targets Tumour-Specific Mutant Antigens. *Nature* 2014, 515, 577-581.
(46) Castle, J. C.; Kreiter, S.; Diekmann, J.; Löwer, M.; van de Roemer, N.; de Graaf, J.; Selmi, A.; Diken, M.; Boegel, S.; Paret, C.; et al. Exploiting the Mutanome for Tumor Vaccination. *Cancer Res.* 2012, 72, 1081-1091.
(47) Kim, K.; Skora, A. D.; Li, Z.; Liu, Q.; Tam, A. J.; Blosser, R. L.; Diaz, L. a; Papadopoulos, N.; Kinzler, K. W.; Vogelstein, B.; et al. Eradication of Metastatic Mouse Cancers Resistant to Immune Checkpoint Blockade by Suppression of Myeloid-Derived Cells. *Proc. Natl. Acad. Sci. U.S.A.* 2014, 111, 11774-11779.
(48) Gulukota, K.; Sidney, J.; Sette, a; DeLisi, C. Two Complementary Methods for Predicting Peptides Binding Major Histocompatibility Complex Molecules. *J. Mol. Biol.* 1997, 267, 1258-1267.
(49) Ernst, B.; Lee, D.; Chang, J. M.; Sprent, J.; Surh, C. D.; Cd, I. The Peptide Ligands Mediating Positive Selection in the Thymus Control T Cell Survival and Homeostatic Proliferation in the Periphery. 1999, 11, 173-181.
(50) Dummer, W.; Ernst, B.; Leroy, E.; Surh, C. D.; Lee, D. Autologous Regulation of Naive T Cell Homeostasis Within the T Cell Compartment. *J. Immunol.* 2001, 166, 2460-2468.
(51) Wu, Z.; Bensinger, S. J.; Zhang, J.; Chen, C.; Yuan, X.; Huang, X.; Markmann, J. F.; Kassaee, A.; Rosengard, B. R.; Hancock, W. W.; et al. Homeostatic Proliferation Is a Barrier to Transplantation Tolerance. *Nat. Med.* 2004, 10, 87-92.
(52) Klebanoff, C. a; Khong, H. T.; Antony, P. a; Palmer, D. C.; Restifo, N P Sinks, Suppressors and Antigen Presenters: How Lymphodepletion Enhances T Cell-Mediated Tumor Immunotherapy. *Trends Immunol.* 2005, 26, 111-117.
(53) Wrzesinski, C.; Paulos, C. M.; Kaiser, A.; Muranski, P.; Palmer, D. C.; Gattinoni, L.; Yu, Z.; Rosenberg, S. a; Restifo, N. P. Increased Intensity Lymphodepletion Enhances Tumor Treatment Efficacy of Adoptively Transferred Tumor-Specific T Cells. *J. Immunother.* 2010, 33, 1-7.
(54) Gattinoni, L.; Finkelstein, S. E.; Klebanoff, C. a; Antony, P. a; Palmer, D. C.; Spiess, P. J.; Hwang, L. N.; Yu, Z.; Wrzesinski, C.; Heimann, D. M.; et al. Removal of Homeostatic Cytokine Sinks by Lymphodepletion Enhances the Efficacy of Adoptively Transferred Tumor-Specific CD8+ T Cells. *J. Exp. Med.* 2005, 202, 907-912.
(55) Alanio, C.; Lemaitre, F.; Law, H. K. W.; Hasan, M.; Albert, M. L. Enumeration of Human Antigen-Specific Naive CD8+ T Cells Reveals Conserved Precursor Frequencies. *Blood* 2010, 115, 3718-3725.
(56) Lu, X.; Jiang, X.; Liu, R.; Zhao, H.; Liang, Z. Adoptive Transfer of pTRP2-Specific CTLs Expanding by Bead-Based Artificial Antigen-Presenting Cells Mediates Anti-Melanoma Response. *Cancer Lett.* 2008, 271, 129-139.
(57) Cobbold, M.; Khan, N.; Pourghcysari, B.; Tauro, S.; McDonald, D.; Osman, H.; Assenmacher, M.; Billingham, L.; Steward, C.; Crawley, C.; et al. Adoptive Transfer of Cytomegalovirus-Specific CTL to Stem Cell Transplant Patients after Selection by HLA-Peptide Tetramers. *J. Exp. Med.* 2005, 202, 379-386.
(58) Yee, C.; Savage, P. a; Lee, P. P.; Davis, M. M.; Greenberg, P. D. Isolation of High Avidity Melanoma-Reactive CTL from Heterogeneous Populations Using Peptide-MHC Tetramers. *J. Immunol.* 1999, 162, 2227-2234.
(59) Bouquié, R.; Bonnin, A.; Bernardeau, K.; Khammari, A.; Dréno, B.; Jotereau, F.; Labarrière, N.; Lang, F. A Fast and Efficient HLA Multimer-Based Sorting Procedure That Induces Little Apoptosis to Isolate Clinical Grade Human Tumor Specific T Lymphocytes. *Cancer Immunol. Immunother.* 2009, 58, 553-566.
(60) Cebecauer, M.; Guillaume, P.; Hozak, P.; Mark, S.; Everett, H.; Schneider, P.; Luescher, I. F. Soluble MHC-Peptide Complexes Induce Rapid Death of CD8+ CTL. *J. Immunol.* 2005, 174, 6809-6819.
(61) Guillaume, P.; Legler, D. F.; Boucheron, N.; Doucey, M.-A.; Cerottini, J.-C.; Luescher, I. F. Soluble Major Histocompatibility Complex-Peptide Octamers with Impaired CD8 Binding Selectively Induce Fas-Dependent Apoptosis. *J. Biol. Chem.* 2003, 278, 4500-4509.
(62) Wölfl, M.; Greenberg, P. D. Antigen-Specific Activation and Cytokine-Facilitated Expansion of Naive, Human CD8+ T Cells. *Nat. Protoc.* 2014, 9, 950-966.
(63) Mackensen, A.; Meidenbauer, N.; Vogl, S.; Laumer, M.; Berger, J.; Andreesen, R. Phase I Study of Adoptive T-Cell Therapy Using Antigen-Specific CD8+ T Cells for the Treatment of Patients with Metastatic Melanoma. *J. Clin. Oncol.* 2006, 24, 5060-5069.
(64) Chapuis, A.; Ragnarsson, G. Transferred WT1-Reactive CD8+ T Cells Can Mediate Antileukemic Activity and Persist in Post-Transplant Patients. *Sci. Transl. Med.* 2013, 27.
(65) Dudley, M. E.; Wunderlich, J.; Nishimura, M. I.; Yu, D.; Yang, J. C.; Topalian, S. L.; Schwartzentruber, D. J.; Hwu, P.; Marincola, F. M.; Sherry, R.; et al. Adoptive Transfer of Cloned Melanoma-Reactive T Lymphocytes for the Treatment of Patients with Metastatic Melanoma. *J. Immunother.* 2001, 24, 363-373.
(66) Oelke, M.; Moehrle, U.; Chen, J.; Behringer, D.; Cerundolo, V.; Lindemann, A.;
Mackensen, A. Generation and Purification of CD8+ Melan-A-Specific Cytotoxic T Lymphocytes for Adoptive Transfer in Tumor Immunotherapy Generation and Purification of CD8 □Melan-A-Specific Cytotoxic T Lymphocytes for Adoptive Transfer in Tumor Immunotherapy 1. 2005, 1997-2005.

REFERENCES FOR WHOLE APPLICATION
EXCEPT EXAMPLE 2

(1) Restifo, N. P.; Dudley, M. E.; Rosenberg, S. Nat. Rev. Immunol. 2012, 12, 269-281.
(2) Dudley, M. E.; Rosenberg, S. Nat. Rev. Cancer 2003, 3, 666-675.
(3) Yee, C. Immunol. Rev. 2014, 257, 250-263.
(4) Itzhaki, O.; Hovav, E.; Ziporen, Y.; Levy, D.; Kubi, A.; Zikich, D.; Hershkovitz, L.; Treves, A. J.; Shalmon, B.; Zippel, D.; Markel, G.; Shapira-frommer, R.; Schachter, J.; J, M. J. B. J Immunother. 2011, 34, 212-220.
(5) Rizzuto, G. a; Merghoub, T.; Hirschhorn-Cymerman, D.; Liu, C.; Lesokhin, A. M.; Sahawneh, D.; Zhong, H.; Panageas, K. S.; Perales, M.-A.; Altan-Bonnet, G.; Wolchok, J. D.; Houghton, A. N. J. Exp. Med. 2009, 206, 849-866.
(6) Jenkins, M. K.; Chu, H. H.; McLachlan, J. B.; Moon, J. J. Annu. Rev. Immunol. 2010, 28, 275-294.
(7) Jenkins, M. K.; Moon, J. J. J. Immunol. 2012, 188, 4135-4140.

(8) Klebanoff, C. a; Gattinoni, L.; Palmer, D. C.; Muranski, P.; Ji, Y.; Hinrichs, C. S.; Borman, Z. a; Kerkar, S. P.; Scott, C. D.; Finkelstein, S. E.; Rosenberg, S. a; Restifo, N. P. Clin. Cancer Res. 2011, 17, 5343-5352.

(9) Wen, F.; Thisted, R. 2012, 172-178.

(10) Besser, M. J.; Shapira-Frommer, R.; Treves, A. J.; Zippel, D.; Itzhaki, O.; Hershkovitz, L.; Levy, D.; Kubi, A.; Hovav, E.; Chermoshniuk, N.; Shalmon, B.; Ilardan, I.; Catane, R.; Markel, G.; Apter, S.; Ben-Nun, A.; Kuchuk, I.; Shimoni, A.; Nagler, A.; Schachter, J. Clin. Cancer Rcs. 2010, 16, 2646-2655.

(11) Chapuis, A.; Ragnarsson, G. Sci. Transl., 2013, 27.

(12) Ernst, B.; Lee, D.; Chang, J. M.; Sprent, J.; Surh, C. D.; Cd, I. 1999, 11, 173-181.

(13) Dummer, W.; Ernst, B.; Leroy, E.; Surh, C. D.; Lee, D. J. Immunol. 2001, 166, 2460-2468.

(14) Wu, Z.; Bensinger, S. J.; Zhang, J.; Chen, C.; Yuan, X.; Huang, X.; Markmann, J. F.; Kassaee, A.; Rosengard, B. R.; Hancock, W. W.; Sayegh, M. H.; Turka, L. a. Nat. Med. 2004, 10, 87-92.

(15) Perica, K.; De Leon Medero, A.; Durai, M.; Chiu, Y. L.; Bieler, J. G.; Sibener, L.; Niemöller, M.; Assenmacher, M.; Richter, A.; Edidin, M.; Oelke, M.; Schneck, J. Nanomedicine 2013, 10, 119-129.

(16) Perica, K.; Tu, A.; Richter, A.; Bieler, J. U.; Edidin, M.; Schneck, J. P. ACS Nano 2014.

(17) Smith-Garvin, J. E.; Koretzky, G. a; Jordan, M. S. Annu. Rev. Immunol. 2009, 27, 591-619.

(18) Sarkar, S.; Teichgräber, V.; Kalia, V.; Polley, A.; Masopust, D.; Harrington, L. E.; Ahmed, R.; Wherry, E. J. J. Immunol. 2007, 179, 6704-6714.

(19) Oelke, M.; Maus, M. V; Didiano, D.; June, C. H.; Mackensen, A.; Schneck, J. P. Nat. Med. 2003, 9, 619-624.

(20) Seliger, B. Cancer Immunol. Immunother. 2008, 57, 1719-1726.

(21) Kaluza, K. M.; Thompson, J. M.; Kottke, T. J.; Flynn Gilmer, H. C.; Knutson, D. L.; Vile, R. G. Int. J. Cancer 2012, 131, 844-854.

(22) Jensen, S. M.; Twitty, C. G.; Maston, L. D.; Antony, P. a; Lim, M.; Hu, H.-M.; Petrausch, U.; Restifo, N. P.; Fox, B. a. J. Immunol. 2012, 189, 767-776.

(23) Kaluza, K. M.; Kottke, T.; Diaz, R. M.; Rommelfanger, D.; Thompson, J.; Vile, R. Hum. Gene Ther. 2012, 23, 1054-1064.

(24) Klebanoff, C. a; Khong, H. T.; Antony, P. a; Palmer, D. C.; Restifo, N. P. Trends Immunol. 2005, 26, 111-117.

(25) Wrzesinski, C.; Paulos, C. M.; Kaiser, A.; Muranski, P.; Palmer, D. C.; Gattinoni, L.; Yu, Z.; Rosenberg, S. a; Restifo, N. P. J. Immunother. 2010, 33, 1-7.

(26) Gattinoni, L.; Finkelstein, S. E.; Klebanoff, C. a; Antony, P. a; Palmer, D. C.; Spiess, P. J.; Hwang, L. N.; Yu, Z.; Wrzesinski, C.; Heimann, D. M.; Surh, C. D.; Rosenberg, S. a; Restifo, N. P. J. Exp. Med. 2005, 202, 907-912.

(27) Alanio, C.; Lemaitre, F.; Law, H. K. W.; Hasan, M.; Albert, M. L. Blood 2010, 115, 3718-3725.

(28) Lu, X.; Jiang, X.; Liu, R.; Thao, H.; Liang, Z. Cancer Lett. 2008, 271, 129-139.

(29) Cobbold, M.; Khan, N.; Pourgheysari, B.; Tauro, S.; McDonald, D.; Osman, H.; Assenmacher, M.; Billingham, L.; Steward, C.; Crawley, C.; Olavarria, E.; Goldman, J.; Chakraverty, R.; Mahendra, P.; Craddock, C.; Moss, P. a H. J. Exp. Med. 2005, 202, 379-386.

(30) Yee, C.; Savage, P. a; Lee, P. P.; Davis, M. M.; Greenberg, P. D. J. Immunol. 1999, 162, 2227-2234.

(31) Bouquié, R.; Bonnin, A.; Bernardeau, K.; Khammari, A.; Dréno, B.; Jotereau, F.; Labarrière, N.; Lang, F. Cancer Immunol. Immunother. 2009, 58, 553-566.

(32) Cebecauer, M.; Guillaume, P.; Hozák, P.; Mark, S.; Everett, H.; Schneider, P.; Luescher, I. F. J. Immunol. 2005, 174, 6809-6819.

(33) Guillaume, P.; Legler, D. F.; Boucheron, N.; Doucey, M.-A.; Cerottini, J.-C.; Luescher, I. F. J. Biol. Chem. 2003, 278, 4500-4509.

(34) Morgan, R. A.; Chinnasamy, N.; Abate-daga, D.; Gros, A.; Robbins, P. F.; Zheng, Z.; Dudley, M. E.; Feldman, S. A.; Yang, J. C.; Sherry, R. M.; Phan, G. Q.; Hughes, M. S.; Kammula, U. S.; Miller, A. D.; Hessman, C. J.; Stewart, A. A.; Restifo, N. P.; Quezado, M. M.; Alimchandani, M.; Rosenberg, A. Z.; Nath, A.; Wang, T.; Bielekova, B.; Wuest, S. C.; Akula, N.; Mcmahon, F. J.; Wilde, S.; Mosetter, B.; Schendel, D. J.; Laurencot, C. M.; Rosenberg, S. A. J. Immunother. 2013, 36, 133-151.

(35) Hundcr, N. N.; Wallen, H.; Cao, J.; Hendricks, D. W.; Reilly, J. Z.; Rodmyrc, R.; Jungbluth, A.; Gnjatic, S.; Thompson, J. a; Yee, C. N. Engl. J. Med. 2008, 358, 2698-2703.

(36) Chapuis, A.; Ragnarsson, G. Sci. Transl. 2013, 27.

(37) Mackensen, A.; Meidenbauer, N.; Vogl, S.; Laumer, M.; Berger, J.; Andreesen, R. J. Clin. Oncol. 2006, 24, 5060-5069.

(38) Dudley, M. E.; Wunderlich, J.; Nishimura, M. I.; Yu, D.; Yang, J. C.; Topalian, S. L.; Schwartzentruber, D. J.; Hwu, P.; Marincola, F. M.; Sherry, R.; Leitman, S. F.; Rosenberg, S. a. J. Immunother. 2001, 24, 363-373.

(39) Wölf, M.; Greenberg, P. D. Nat. Protoc. 2014, 9, 950-966.

The invention claimed is:

1. A method for treating a cancer patient, comprising:
administering a composition comprising cytotoxic T cells specific for one or more tumor-associated peptide antigens to the cancer patient, wherein at least 10% of the cytotoxic T cells in the composition are specific for the tumor-associated peptide antigen(s), the composition prepared by a process comprising:
providing a sample comprising T cells from a patient or donor,
contacting said sample with a population of nanoparticles which are paramagnetic and comprise on their surfaces: (1) MHC-class I molecular complexes dimerized by an Ig hinge region, and presenting tumor-associated peptide antigens and (2) a lymphocyte costimulatory ligand for CD28, wherein the paramagnetic particles are from about 10 nm to about 500 nm in diameter,
placing a magnetic field in proximity to the paramagnetic particles, and separating cells associated with the paramagnetic particles from cells not associated with the paramagnetic particles,
recovering cells associated with the paramagnetic particles, and
expanding the recovered cells in culture for 1 to 3 weeks to prepare the composition.

2. The method of claim 1, wherein at least 20% of the cytotoxic T cells in the composition are specific for the tumor-associated peptide antigen(s).

3. The method of claim 1, wherein the cancer patient has a hematological malignancy.

4. The method of claim 1, wherein the sample comprising T cells is isolated by leukapheresis.

5. The method of claim 1, wherein the sample comprises naive T cells.

6. The method of claim 5, wherein the naive T cells are recovered associated with the paramagnetic particles.

7. The method of claim 1 further comprising depleting CD4+ cells from the sample comprising T cells.

8. The method of claim 1, wherein the MHC class I molecular complex corresponds to an HLA-A, HLA-B, HLA-C, or HLA-E gene.

9. The method of claim 1, wherein the MHC class I molecular complex comprises HLA-A2 α chains.

10. The method of claim 1, wherein the lymphocyte costimulatory ligand for CD28 is an agonistic antibody or an antigen-binding fragment thereof against CD28.

11. The method of claim 10, wherein the antibody or the antigen-binding fragment thereof is a monoclonal antibody which may be humanized, a F(ab')2, a Fab, an scFv, or a single chain antibody.

12. The method of claim 1, wherein the population of nanoparticles comprises a plurality of particle subpopulations, each particle subpopulation presenting a different tumor-associated peptide antigen.

13. The method of claim 12, wherein the subpopulations of particles present from 3 to 10 different peptide antigens.

14. The method of claim 1, wherein the cytotoxic T cells are specific for multiple tumor associated antigens.

15. The method of claim 1, wherein the paramagnetic particles are from about 20 nm to about 200 nm in diameter.

16. The method of claim 1, wherein the composition comprises at least about $10^6$ T cells specific for the one or more tumor-associated peptide antigens.

17. The method of claim 1, wherein the composition comprises at least about $10^7$ cytotoxic T cells specific for the one or more tumor-associated peptide antigens.

18. The method of claim 1, wherein the T cells are expanded in culture in the presence of cytokines.

19. The method of claim 1, wherein the composition comprises effector memory T cells.

20. The method of claim 18, wherein cells are expanded in culture for 10 to 14 days.

* * * * *

UNITED STATES PATENT AND TRADEMARK OFFICE
CERTIFICATE OF CORRECTION

PATENT NO. : 10,098,939 B2
APPLICATION NO. : 15/790787
DATED : October 16, 2018
INVENTOR(S) : Jonathan Schneck et al.

Page 1 of 1

It is certified that error appears in the above-identified patent and that said Letters Patent is hereby corrected as shown below:

In the Specification

On Column 1, Line 3, please add the following subheading and paragraph after the Title, and before the subheading "TECHNICAL FIELD":
-- STATEMENT REGARDING FEDERALLY SPONSORED RESEARCH OR DEVELOPMENT
This invention was made with government support under CA108835, awarded by the National Institutes of Health. The government has certain rights in the invention. --

Signed and Sealed this
Eighteenth Day of August, 2020

Andrei Iancu
*Director of the United States Patent and Trademark Office*